United States Patent
Zipnick

(10) Patent No.: US 10,265,187 B2
(45) Date of Patent: Apr. 23, 2019

(54) SPINNER BODY

(71) Applicant: ARTHRODISC, L.L.C., Park City, UT (US)

(72) Inventor: Richard I. Zipnick, Park City, UT (US)

(73) Assignee: ARTHRODISC, L.L.C., Park City, UT (US)

( * ) Notice: Subject to any disclaimer, the term of this patent is extended or adjusted under 35 U.S.C. 154(b) by 336 days.

(21) Appl. No.: 13/667,551

(22) Filed: Nov. 2, 2012

(65) Prior Publication Data

US 2013/0150969 A1 Jun. 13, 2013

Related U.S. Application Data

(63) Continuation-in-part of application No. 13/605,756, filed on Sep. 6, 2012, now Pat. No. 9,005,296, and a
(Continued)

(51) Int. Cl.
*A61F 2/44* (2006.01)
*A61B 17/32* (2006.01)
(Continued)

(52) U.S. Cl.
CPC .......... *A61F 2/44* (2013.01); *A61B 17/32002* (2013.01); *A61B 17/320016* (2013.01); *A61B 17/3421* (2013.01); *A61B 17/3476* (2013.01); *A61F 2/442* (2013.01); *A61F 2/4425* (2013.01); *A61F 2/4455* (2013.01); *A61B 1/3135* (2013.01);
(Continued)

(58) Field of Classification Search
CPC ........ A61F 2002/4435; A61F 2002/443; A61F 2002/30517; A61F 2/44; A61F 2/442; A61F 2/4425; A61F 2/4455; A61F 2002/30769; A61F 2002/30771; A61F 2002/30777; A61F 2002/30772; A61F 2002/3078; A61F 2002/30784; A61F 2002/3079;
(Continued)

(56) References Cited

U.S. PATENT DOCUMENTS 5,683,394 A * 11/1997 Rinner .................. A61F 2/4455 606/247
6,322,591 B1 * 11/2001 Ahrens .................. A61B 17/72 606/62

(Continued)

*Primary Examiner* — Zade Coley
*Assistant Examiner* — Jessica Weiss
(74) *Attorney, Agent, or Firm* — Maschoff Brennan

(57) ABSTRACT

An intervertebral implant can include a housing having a first end and second end with a top side and bottom side therebetween, with at least one engagement opening in the top side and/or bottom side, the implant having a first dimension from the top side to the bottom side; a shaft rotatably located within the housing and having a shaft head exposed through an end opening in the first end, the shaft head having a tool coupling member; the cam mechanism operably coupled with the shaft such that rotation of the shaft rotates the cam mechanism; and at least one engaging surface operably coupled to the cam mechanism such that rotation of the shaft protrudes and/or retracts each engaging surface through an engagement opening, wherein when each engaging surface protrudes through the engagement opening, the implant has a second dimension that is greater than the first dimension.

26 Claims, 21 Drawing Sheets

Related U.S. Application Data continuation-in-part of application No. 13/605,752, filed on Sep. 6, 2012, now abandoned, and a continuation-in-part of application No. 13/478,870, filed on May 23, 2012, now Pat. No. 9,155,553, and a continuation-in-part of application No. 13/370,925, filed on Feb. 10, 2012, now abandoned, and a continuation-in-part of application No. 13/199,324, filed on Aug. 26, 2011, now Pat. No. 8,961,605, and a continuation-in-part of application No. 11/827,519, filed on Jul. 12, 2007, now Pat. No. 8,753,394, and a continuation-in-part of application No. 13/065,291, filed on Mar. 18, 2011, now Pat. No. 8,795,367, which is a continuation-in-part of application No. 11/804,838, filed on May 21, 2007, now Pat. No. 7,909,872, which is a continuation-in-part of application No. 11/638,652, filed on Dec. 12, 2006, now Pat. No. 7,883,542, which is a continuation-in-part of application No. 11/472,060, filed on Jun. 21, 2006, now Pat. No. 7,879,099, which is a continuation-in-part of application No. 11/404,938, filed on Apr. 14, 2006, now Pat. No. 7,727,279, which is a continuation-in-part of application No. 11/351,665, filed on Feb. 10, 2006, now abandoned, which is a continuation-in-part of application No. 11/299,395, filed on Dec. 12, 2005, now abandoned, and a continuation-in-part of application No. 11/241,143, filed on Sep. 30, 2005, now abandoned, which is a continuation-in-part of application No. 11/145,372, filed on Jun. 3, 2005, now abandoned.

(60) Provisional application No. 61/554,589, filed on Nov. 2, 2011, provisional application No. 61/554,600, filed on Nov. 2, 2011, provisional application No. 61/554,616, filed on Nov. 2, 2011.

(51) Int. Cl.
```
A61B 17/34      (2006.01)
A61B 1/313      (2006.01)
A61F 2/30       (2006.01)
A61F 2/46       (2006.01)
A61B 17/70      (2006.01)
A61B 17/00      (2006.01)
A61B 17/3211    (2006.01)
A61B 17/88      (2006.01)
A61B 17/86      (2006.01)
A61B 90/00      (2016.01)
```

(52) U.S. Cl.
CPC ... *A61B 17/320068* (2013.01); *A61B 17/3468* (2013.01); *A61B 17/7059* (2013.01); *A61B 17/86* (2013.01); *A61B 17/888* (2013.01); *A61B 2017/00261* (2013.01); *A61B 2017/320044* (2013.01); *A61B 2017/32113* (2013.01); *A61B 2090/0801* (2016.02); *A61F 2/3094* (2013.01); *A61F 2/30771* (2013.01); *A61F 2/447* (2013.01); *A61F 2/4611* (2013.01); *A61F 2002/3055* (2013.01); *A61F 2002/30112* (2013.01); *A61F 2002/30153* (2013.01); *A61F 2002/30205* (2013.01); *A61F 2002/30224* (2013.01); *A61F 2002/30233* (2013.01); *A61F 2002/30253* (2013.01); *A61F 2002/30271* (2013.01); *A61F 2002/30285* (2013.01); *A61F 2002/30286* (2013.01); *A61F 2002/30331* (2013.01); *A61F 2002/30393* (2013.01); *A61F 2002/30398* (2013.01); *A61F 2002/30401* (2013.01); *A61F 2002/30428* (2013.01); *A61F 2002/30507* (2013.01); *A61F 2002/30517* (2013.01); *A61F 2002/30528* (2013.01); *A61F 2002/30545* (2013.01); *A61F 2002/30553* (2013.01); *A61F 2002/30578* (2013.01); *A61F 2002/30579* (2013.01); *A61F 2002/30594* (2013.01); *A61F 2002/30601* (2013.01); *A61F 2002/30604* (2013.01); *A61F 2002/30772* (2013.01); *A61F 2002/30818* (2013.01); *A61F 2002/30822* (2013.01); *A61F 2002/30823* (2013.01); *A61F 2002/30831* (2013.01); *A61F 2002/30841* (2013.01); *A61F 2002/30881* (2013.01); *A61F 2002/30883* (2013.01); *A61F 2002/30884* (2013.01); *A61F 2002/4475* (2013.01); *A61F 2002/4677* (2013.01); *A61F 2310/00011* (2013.01); *A61F 2310/00179* (2013.01)

(58) Field of Classification Search
CPC .. A61F 2002/30792; A61F 2002/30813; A61F 2002/30838; A61F 2002/3084
USPC .......................................... 623/17.11–17.16
See application file for complete search history.

(56) References Cited

U.S. PATENT DOCUMENTS

| | | | | |
|---|---|---|---|---|
| 6,527,803 B1* | 3/2003 | Crozet | ................. | A61F 2/442 |
| | | | | 606/31 |
| 6,770,096 B2* | 8/2004 | Bolger et al. | ............. | A61F 2/44 |
| | | | | 623/17.11 |
| 6,773,460 B2* | 8/2004 | Jackson | ................ | A61F 2/4455 |
| | | | | 623/17.11 |
| 6,835,206 B2* | 12/2004 | Jackson | ................ | A61F 2/4455 |
| | | | | 623/17.11 |
| 2005/0049590 A1* | 3/2005 | Alleyne | ................ | A61F 2/442 |
| | | | | 623/17.11 |
| 2005/0060034 A1* | 3/2005 | Berry | ........................ | A61F 2/44 |
| | | | | 623/17.11 |
| 2005/0101960 A1* | 5/2005 | Fiere | ................. | A61B 17/7059 |
| | | | | 623/17.11 |
| 2007/0150059 A1* | 6/2007 | Ruberte | ................ | A61F 2/441 |
| | | | | 623/17.12 |
| 2012/0277865 A1* | 11/2012 | Trieu | ..................... | A61F 2/442 |
| | | | | 623/17.16 |
| 2014/0277461 A1* | 9/2014 | Nebosky | ................... | A61F 2/44 |
| | | | | 623/17.11 |

* cited by examiner

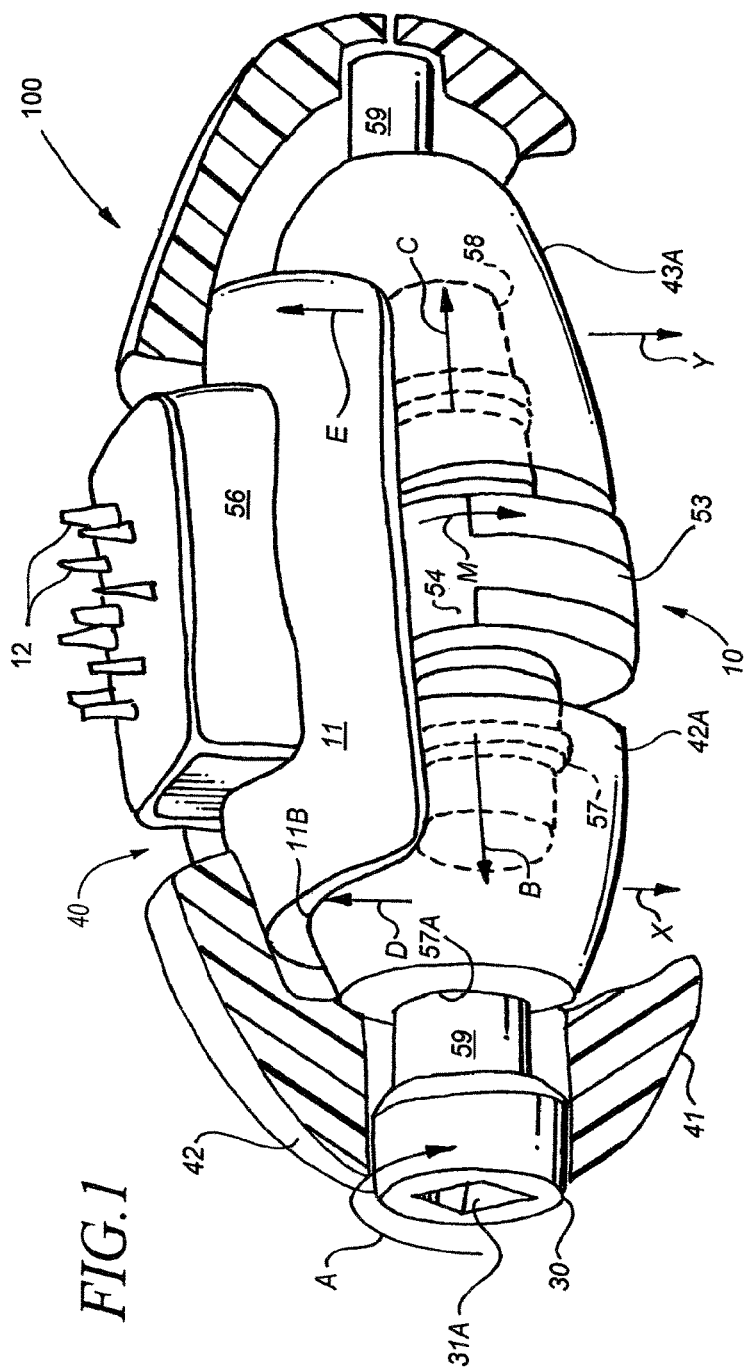
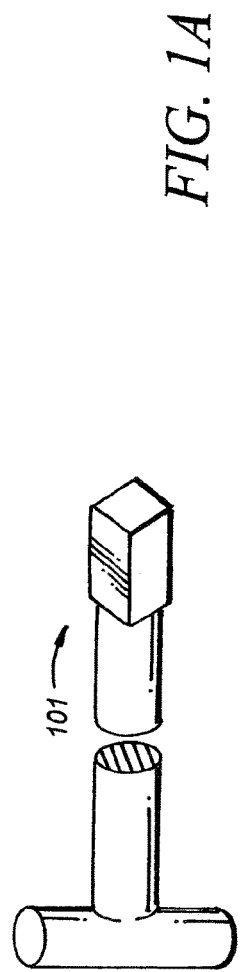
FIG. 1
FIG. 1A

FIG. 10
FIG. 12
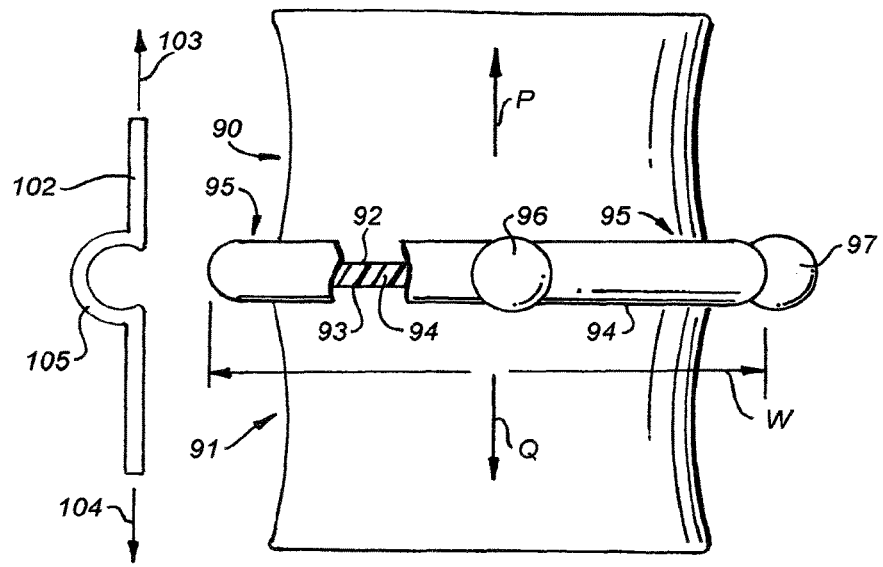
FIG. 11
FIG. 9
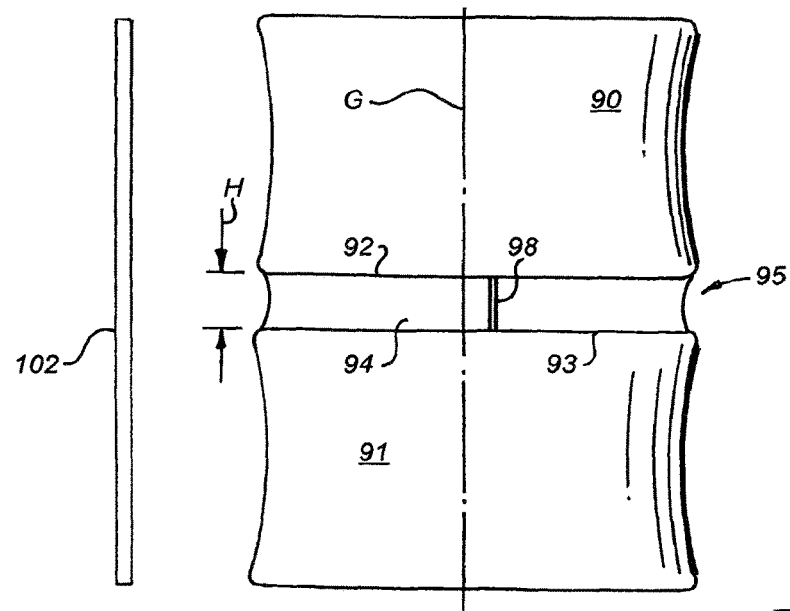

Fig. 20
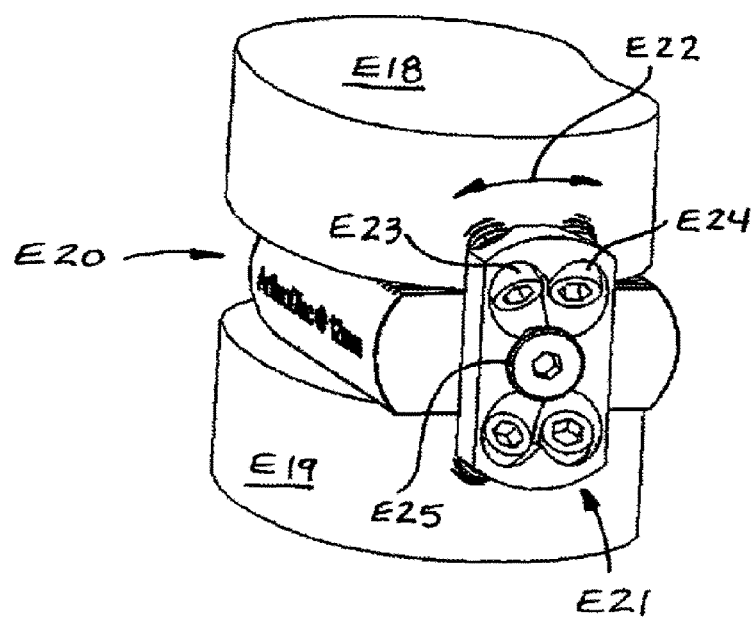
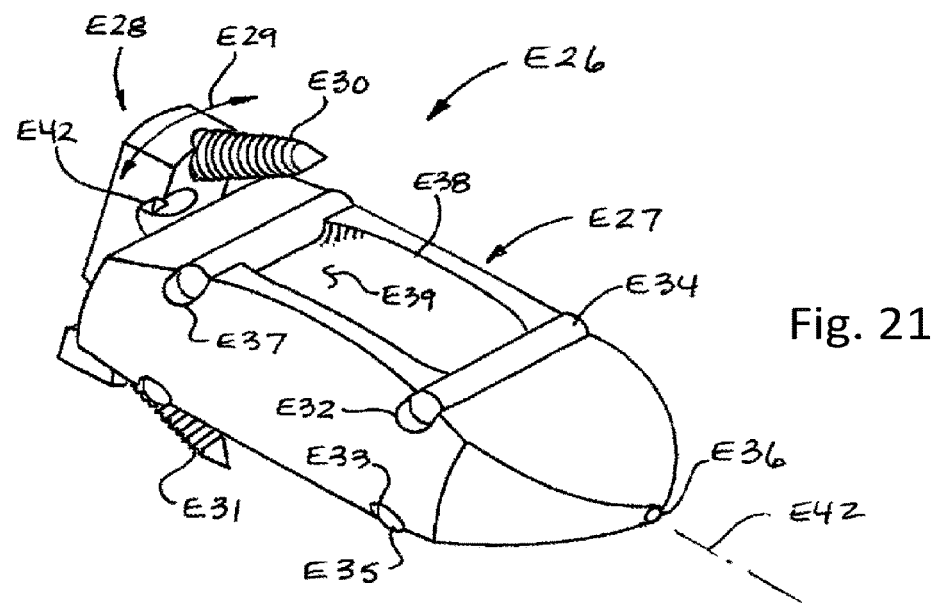
Fig. 21

Fig. 22
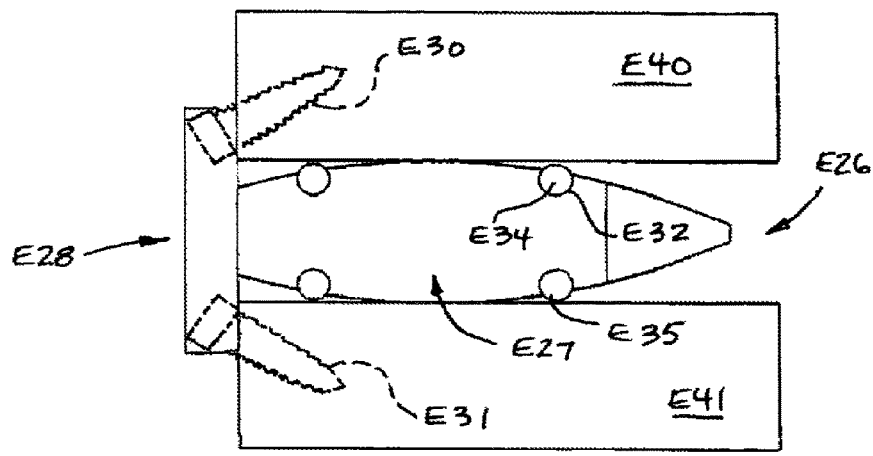
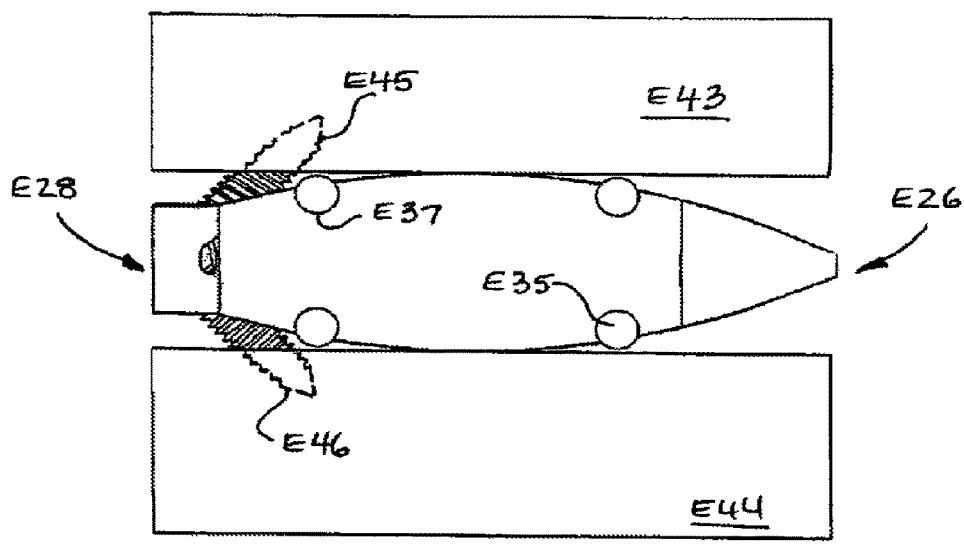
Fig. 23

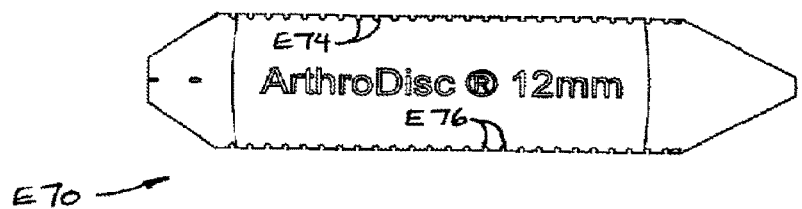
Fig. 25
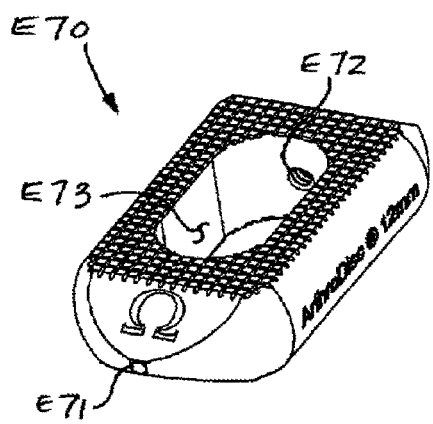
Fig. 24
Fig. 27
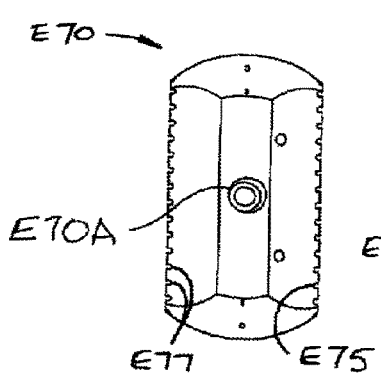
Fig. 26
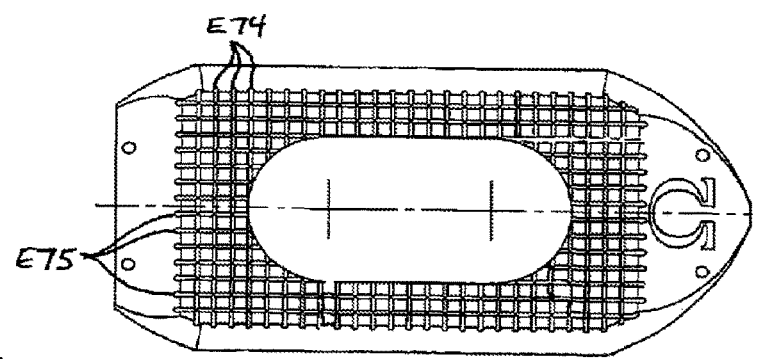

SPINNER BODY

CROSS-REFERENCE TO RELATED APPLICATIONS

This patent application claims the benefit of U.S. Provisional Application Ser. No. 61/554,589, filed Nov. 2, 2011, U.S. Provisional Application Ser. No. 61/554,600, filed Nov. 2, 2011, and U.S. Provisional Application Ser. No. 61/554,616, filed Nov. 2, 2011, which provisional applications are each incorporated herein by specific reference in their entirety. This application is also a continuation-in-part of U.S. patent application Ser. No. 13/605,756, filed Sep. 6, 2012 now U.S. Pat. No. 9,005,296. This application is also a continuation-in-part of U.S. patent application Ser. No. 13/605,752, filed Sep. 6, 2012. This application is also a continuation-in-part of U.S. patent application Ser. No. 13/478,870 filed May 23, 2012 now U.S. Pat. No. 9,155,553. This application is also a continuation-in-part of U.S. patent application Ser. No. 13/370,925 filed Feb. 10, 2012. This application is also a continuation-in-part of U.S. patent application Ser. No. 13/199,324 filed Aug. 26, 2011 now U.S. Pat. No. 8,961,605. This application is also a continuation-in-part of U.S. patent application Ser. No. 11/827,519, filed Jul. 12, 2007 now U.S. Pat. No. 8,753,394. This application is also a continuation-in-part of U.S. patent application Ser. No. 13/065,291, filed Mar. 18, 2011 now U.S. Pat. No. 8,795,367, which is a continuation-in-part of U.S. patent application Ser. No. 11/804,838, filed May 21, 2007, now U.S. Pat. No. 7,909,872, which is a continuation-in-part of U.S. patent application Ser. No. 11/638,652, filed Dec. 12, 2006 now U.S. Pat. No. 7,883,542, which is a continuation-in-part of U.S. patent application Ser. No. 11/472,060, filed Jun. 21, 2006 now U.S. Pat. No. 7,879,099, which is a continuation-in-part of U.S. patent application Ser. No. 11/404,938, filed Apr. 14, 2006 now U.S. Pat. No. 7,727,279, which is a continuation-in-part of U.S. patent application Ser. No. 11/351,665 filed Feb. 10, 2006 now abandoned, which is a continuation-in-part of U.S. patent application Ser. No. 11/299,395 filed Dec. 12, 2005 now abandoned and U.S. patent application Ser. No. 11/351,665 is also a continuation-in-part of U.S. patent application Ser. No. 11/241,143 filed Sep. 30, 2005 now abandoned, which is a continuation-in-part of U.S. patent application Ser. No. 11/145,372, filed Jun. 3, 2005 now abandoned. Each of these applications and patents are incorporated herein by specific reference in their entirety.

BACKGROUND

An intervertebral disc is a soft tissue compartment connecting the vertebrae bones in a spinal column. Each healthy disc consists of two parts, an outer annulus fibrosus (hereinafter "the annulus") and an inner nucleus pulposus (hereinafter "the nucleus"). The annulus completely circumscribes and encloses the nucleus. The annulus is connected to an adjacent associated pair of vertebrae by collagen fibers. The intervertebral disc is an example of a soft tissue compartment adjoining first and second bones (vertebrae) having an initial height and an initial width. Other joints consisting of a soft tissue compartment adjoining at least first and second bones having an initial height and an initial width include the joints of the hand, wrist, elbow, shoulder, foot, ankle, knee, hip, etc.

Typically, when a disc is damaged, the annulus ruptures and the nucleus herniates. Discectomy surgery removes the extruded nucleus, leaving behind the ruptured annulus. The ruptured annulus is, by itself, ineffective in controlling motion and supporting the loads applied by the adjacent pair of vertebrae. With time, the disc flattens, widens, and bulges, compressing nerves and producing pain. Uncontrolled loads are transmitted to each vertebra. Each vertebra tends to grow wider in an attempt to distribute and compensate for higher loads. When a vertebra grows, bone spurs form. The bone spurs further compress nerves, producing pain.

A variety of expandable intervertebral devices are disclosed in the art to replace the intervertebral disc. Such devices are implanted intermediate an adjacent pair of vertebrae, and function to assist the vertebrae. These devices do not assist the intervertebral disc. In fact, in many cases the disc is removed.

Prior art intervertebral devices are either static or dynamic. A static intervertebral device eliminates motion. Static devices are generally square, rectangular, trapezoidal, or box shapes that are immobile. Static devices replace the disc to facilitate bone fusion. The insertion of a static device requires near-total removal of the disc. An adjacent pair of vertebrae ordinarily is contoured to the static device and a bone graft. A static device temporarily maintains the vertebrae immobilized until the bone graft heals. Static devices may, on insertion, initially expand, but their final state is immobile. Core elements with the threads on one portion reversed or oppositely wound from threads on another portion have been frequently utilized to expand immobilization (fusion) devices.

Dynamic devices are configured to be capable of moving. Inserting a dynamic device, such as a total disc prosthesis, requires a near-total removal of disc tissue. A dynamic device ordinarily is inserted to contour to the vertebral bones without a bone graft. Usually the vertebral bones are contoured to the dynamic device. Round, curved, or circular-shaped devices inserted after removing disc tissue or vertebral bone tend to migrate in the intervertebral disc space or subside within the vertebral bone. Dynamic devices are often permanent devices that replace a disc, connect vertebral bones together, and allow movement. Dynamic devices initially may expand. Also, their final state can be mobile.

Other dynamic devices require partial removal of disc tissue. These devices can be inserted within the interior (nucleus) of an intervertebral disc and contour to the vertebral bones. Nucleus devices are generally smaller than devices used as a total disc prosthesis. Nucleus devices often are single part-locking mechanisms. Fixation generally is not used and the device typically migrates within the disc space or subsides in vertebral bones. Other dynamic devices do not have a solid-bearing surface but include liquid or gas.

Other devices and methods function to patch or seal a disc without substantially supporting the vertebrea. Inserting these devices requires the removal of disc tissue. These devices are usually added to the annulus, which causes widening of the annulus, and the device increases the risk of contacting the nerves of the spinal column when the disc is compressed. Still other devices can form a physical barrier with the annulus in order to function, where such a barrier positioned within the annulus can prevent the annulus from healing. Still other devices change the material property of the disc.

Therefore, there remains a need in the art for improved devices and methods for treating injuries, deformations, or other defects in any of the intervertebral discs of the spine.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 is a perspective view illustrating an intervertebral device constructed in accordance with the principles of the invention;

FIG. 1A is a perspective view of a tool that can be utilized in the practice of the invention;

FIGS. 9-12 illustrate various views of intervertebral implants implanted in an intervertebral space between adjacent vertebrae to correct or withdraw a disc herniation, and optionally expanding the vertebrae apart.

FIG. 20 provides a back view of an implanted implant.

FIG. 21 provides a perspective view of the implant of FIG. 20.

FIG. 22 provides a side view of the implant of FIG. 20 being implanted with the wing extended.

FIG. 23 provides a side view of the implant of FIG. 20 being implanted with the wing retracted.

FIG. 24 provides a perspective view of an implant.

FIG. 25 provides a side vie of the implant of FIG. 24.

FIG. 26 provides a top view of the implant of FIG. 24.

FIG. 27 provides an end view of the implant of FIG. 24.

DETAILED DESCRIPTION

Figure 2:
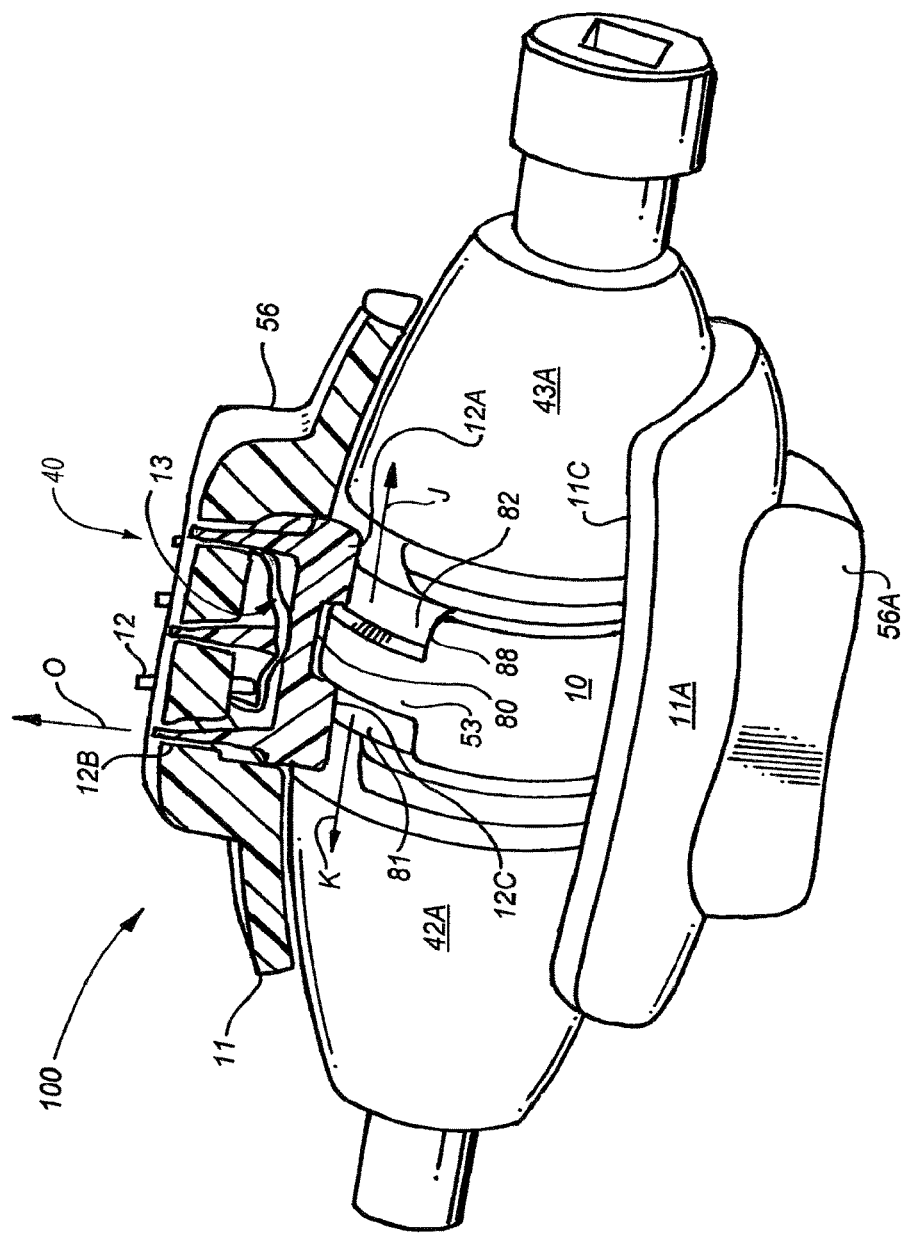
FIG. 2 is a perspective-partial section view of the device of FIG. 1 illustrating additional construction details thereof.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to intervertebral implants that are configured for therapeutic methods, such as to correct spinal alignment and/or to manipulate and revitalize a spinal column disc. The implant devices and methods of implantation may be configured for minimizing or preventing the removal of disc material for implantation into the disc. The implantation method allows for an implant device to be inserted into the disc either through a preexisting rupture or through an opening formed in the front, back, or sides of the disc. Increasing the disc space between the vertebrae bounding the disc or removing disc material can be performed, but often is not necessary to insert the implant device into the disc space. The implant device can be designed to selectively provide contact with the surfaces of adjacent vertebrae, and thereby selectively apply internal traction or other forces acting on the vertebrae to alter the shape of the disc. However, the implant device may only contact one vertebra surface and disc material on the other side between the vertebra and the implant surface in order to apply forces to the vertebral surfaces. In one embodiment, the implant device is configured with a shaft that rotates within a body having an aperture therethrough to selectively expose engaging surfaces of a cam from one or both openings of the aperture.

In one embodiment, the implant device is fabricated by coupling separate housing members of different material or modulus of elasticity through puzzle-shaped coupling members, such as described in the incorporated references.

The method of implantation of the implant device and/or camming of the cam can alter the shape of the disc to withdraw herniations or bulges inwardly in order to relieve pressure on nerves adjacent the disc. Also, the shape of the disc can be altered to draw nuclear hernias back into the interior of the disc and to produce a disc shape that improves functioning of the disc and provides pain relief. The invention also relates to methods of manufacture, implantation, extraction, or other uses of the implant devices.

In one embodiment, the present invention relates to implants having a body with an internal rotatable shaft that operates a cam that is located in an aperture of the body in order to selectively expose engaging surfaces of the cam from one or both openings of the aperture. The cam can be a single-sided cam that only causes protrusion of the engaging surfaces from one opening, or a double-sided cam that causes protrusion of opposing engaging surfaces of the cam from the opposing openings of the aperture.

In one embodiment, the implant includes a housing having a tapered end and blunt opposite end with a rotatable plate that is rotatably attached to the blunt end opposite of the tapered end of the implant housing. The implant can have a housing body with a rectangular cross-sectional profile. Similarly, the rotatable plate can also have a rectangular cross-sectional profile such that the rotatable plate and housing can have the rectangular shapes aligned. As such, the housing and rotatable plate can be in a first position with respect to the housing body such that the rectangular plate and housing body align (e.g., minus sign or "_"). The rotatable plate can be rotatable with respect to the housing body so as to be rotatable to a second position where the rectangular cross-sectional profiles of the plate and housing body are at an angle, such as a 90-degree angle or to form a plus sign (e.g., "+") shape or any angle between aligned and orthogonal. The rotatable plate can be configured to be a bone plate, and can have apertures for fastening to bone such as perimeter surfaces of adjacent vertebrae. However, the housing body and/or rotatable plate may not be perfectly rectangular, but both can have cross-sectional profiles that are elongate in one dimension and short in the other so that the housing and plate can be aligned like a minus sign or staggered like a plus sign. The ends of the elongate dimension can be rounded or squared.

An embodiment of the invention includes an implant device configured to improve the functioning of an intervertebral disc positioned between, contacting, and/or separating a pair of vertebrae in a spine having a longitudinal axis. The implant can be implanted between the vertebrae in order to maintain or increase a height (H) of the space or disc between the vertebrae and thereby to decrease the width (W) of the disc. The implant device can be configured to selectively contact at least one vertebra surface of the pair of vertebrae and expand in the direction of the longitudinal axis to separate the pair of vertebrae along the longitudinal axis of the spine. This can increase the height (H) of the disc or disc space, and decrease perpendicularly the width (W) of the damaged disc to reduce pressure on nerves adjacent said disc. The implant device can include a rotatable shaft configured to turn a cam that is operably coupled to an engaging surface having at least one interlocking engaging protrusion or recess, where one or more engaging surfaces are cooperatively shaped and dimensioned to separate the vertebrae when the cam is rotated.

The shaft can include a body that is configured to turn as a cam. The cam body may be coupled to or integrated with the shaft body. The cam body can include or be coupled to a member that has an engaging surface with at least one interlocking tooth or recess, where the cam body is shaped and dimensioned to separate the vertebrae with the engaging surface when the cam is rotated. The implant device can include a rotatable plate located on an end of the implant housing and coupled to the shaft so as to be configured to turn the shaft and cam system so that the bone-engaging surface can engage the vertebral surface. The cam can include at least one ribbed tooth that interlocks with at least one slot on the bottom of a base. The base can be configured to move unidirectionally, multidirectionally, rotationally, and/or poly-axially when cammed with the cam body. Rotating the cam from a first housed position to at least a second deployed position can deploy (e.g., linearly or arcuately deploy) the engaging surfaces. The implant device can be configured to deploy the engaging surfaces upon rotating the shaft from a first housed position (e.g., the engaging surfaces are housed or retracted) to a second deployed position where the engaging surfaces are protruded or deployed from the housing. The shaft can be rotated so that the engaging surface moves from being inside an aperture in a housing to protruding from the aperture above an outer surface of the housing. The engaging surface is selectively extended from the aperture to protrude past the outer surface of the housing in a measurable amount. The engaging surface can be engaged directly with the vertebral surface or indirectly through disc material between the engaging surface and vertebral surface. The camming and protruding of the engaging surface can be designed to separate the adjacent vertebra and generate negative pressure sufficient to change the shape of the disc. Rotating the cam from a first housed position to at least a second deployed position can also expose a porous material that can be contained within the engaging surface. The porous material can be configured as described herein, and may include an agent that stimulates bone growth so that bone can grow into the porous material or replace the porous material.

FIGS. 1-5 illustrate a disc revitalization device constructed in accordance with the principles of the invention and generally indicated by reference character 100. Disc revitalization device 100 includes a housing having an upper generally semi-oval member 42 and a lower generally semi-oval member 41 that combine to form an oval housing. Shaft 59 is mounted on and inside the housing. The head 30 of shaft 59 includes a fastener head indent (e.g., square or hex) or opening or other indent 31A shaped to contour to and receive slidably the driver end (e.g., square or hexagonally-shaped end) of an elongate tool (e.g., FIG. 1A) used to turn the head 30 of shaft 59. Unitary master cam 10 is fixedly secured to the center of shaft 59, along with externally-threaded member 57 and externally-threaded member 58. Member 57 is received by an internally-threaded aperture in member 42A. Member 58 is received by an internally-threaded aperture in member 43A. Conical members 42A and 43A each have a truncated conical exterior shape and have inner cylindrical openings that can slide along shaft 59 in the directions indicated by arrows B and C, respectively, when members 57 and 58 rotate and displace members 42A and 43A along shaft 59. Members 57 and 58 are oppositely threaded such that when shaft 59 is turned in the direction of arrow A, member 57 turns inside conical member 42A and slidably displaces member 42A along shaft 59 in the direction of arrow B, and member 58 turns inside conical member 43A and slidably displaces member 43A along shaft 59 in the direction of arrow C.

When members 42A and 43A are slidably displaced along shaft 59 in the direction of arrows B and C, respectively, the outer conical surfaces of members 42A and 43A slide over the arcuate inner surface 11B and 11C of arcuate shells 11 and 11A, respectively, and displace shell 11 upwardly away from shaft 59 in the direction of arrows D and E and shell 11A downwardly away from shaft 59 in directions X and Y opposite the directions indicated by arrows D and E. This causes arcuate shells 11 and 11A to move away from each other. By the arcuate shells 11 and 11A moving away from each other, teeth 12 of a bone-engaging surface such as base 12A. Teeth or pins 12 extend outwardly from base 12A (FIG. 2) and are shown in the retracted position within the housing and not exposed from the opening 40 in FIGS. 2 and 4. Base 12A is mounted inside shell 11 beneath and within the head 56 of shell 11. Wave spring 13 contacts an undersurface of head 56 and downwardly displaces base 12A away from the head 56. Wave spring 13 therefore functions to maintain teeth 12 housed and retracted in openings 12B. After extending from openings 12B, the teeth can protrude out of the opening 40. The openings 12B extend through head 56. When teeth 12 are in the retracted position illustrated in FIG. 2, edge 88 of master cam 10 is in the position illustrated in FIG. 2 such that rib 53 engages slot 80 on the bottom of base 12A and prevents base 12A (and shell 11) from moving laterally in the directions indicated by arrows J and K in FIG. 2. When, however, a tool is used to rotate head 30 and shaft 59 in the direction of arrow A, master cam 10 rotates simultaneously with shaft 59 in the direction of arrow M (FIG. 1) until rib 53 turns completely out of slot 80 and smooth cam surface 54 engages and slidably contours to the arcuate bottom 12C of base 12A. When surface 54 engages bottom 12C, surface 54 is flush with adjacent portions of the conical outer surfaces of members 42A and 43A such that bottom 12C of base 12A and bottom 11B of shell 11 are free to slide laterally in the directions of arrows B and C over surface 54 and the outer conical surfaces of members 42A and 43A, and such that bottom 12C of base 12A and bottom 11B of shell 11 are free to rotate or slide in the direction of arrow M (FIG. 1) and in a direction opposite that of arrow M over surface 54 and the outer conical surfaces of members 42A and 43A. This ability of shell 11 and base 12A to move bidirectionally or multidirectionally (i.e., to move polyaxially) by sliding laterally (in the direction of arrows J and K), by sliding forwardly or rotationally (in the direction of arrow M), and by sliding in a direction intermediate said lateral and forward directions facilitates the ability of device 100 to adapt to movement of a vertebra. In addition, as rib 53 is turned out of and exits slot 80, cam surfaces 81 and 82 contact and slidably displace base 12A upwardly in the direction of arrow O (FIG. 2) to compress and flatten wave spring 13 and to displace teeth 12 outwardly through openings 12B such that teeth 12 are in the deployed position illustrated in FIG. 1.

Figure 3:
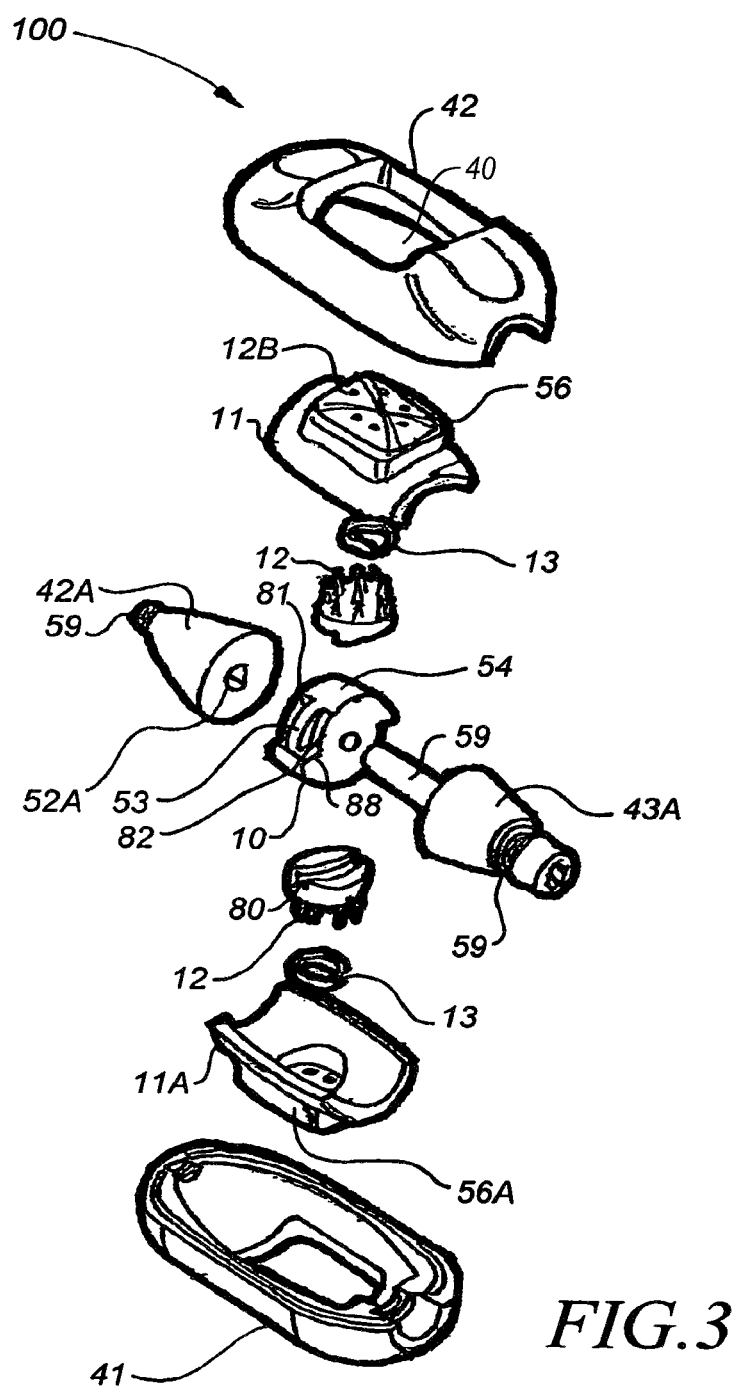
FIG. 3 is an exploded view of certain components of the device of FIG. 1.
Figure 4:
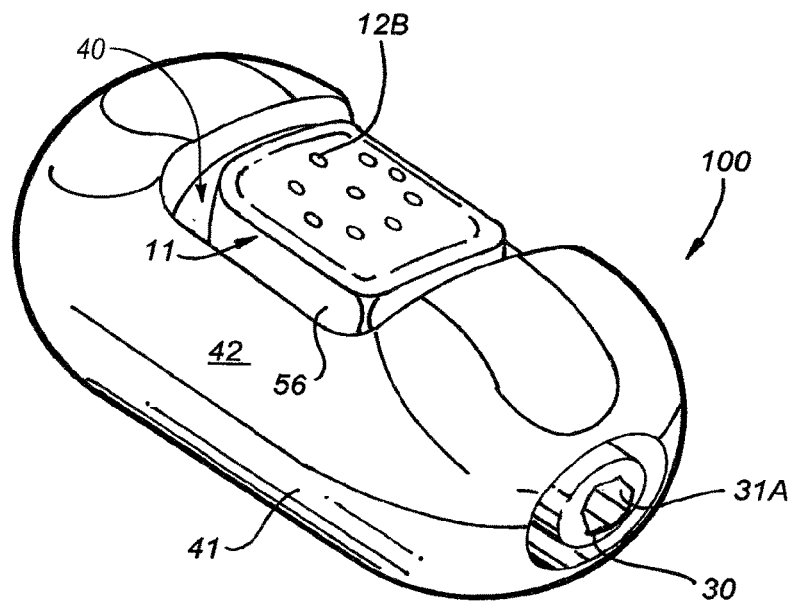
FIG. 4 is a perspective view further illustrating the device of FIG. 1.
Figure 5:
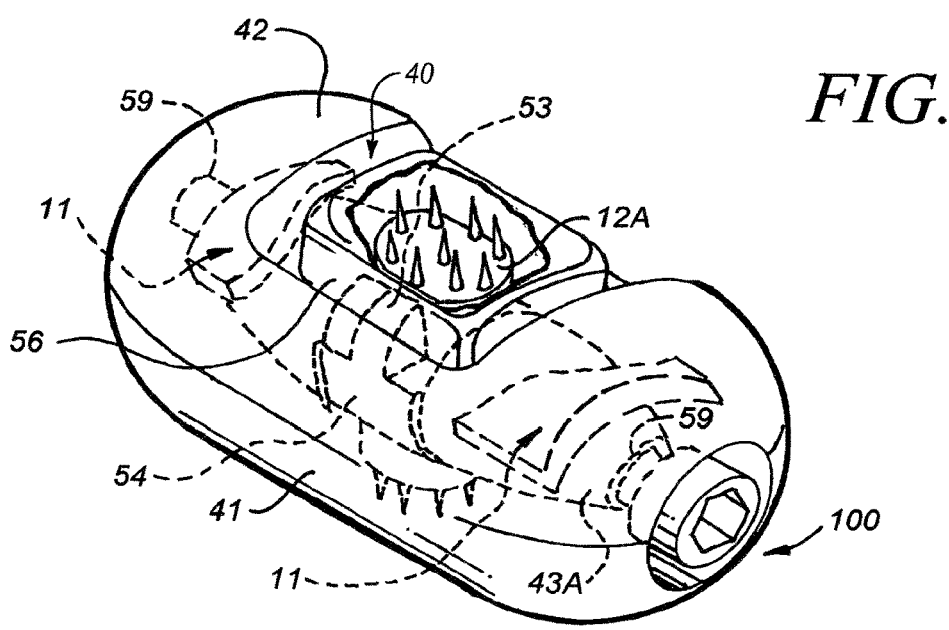
FIG. 5 is a perspective view of the device of FIG. 1 illustrating certain components in ghost outline

As can be seen in FIG. 3, the construction of shell 11A and the base, head 56A, and teeth in shell 11A is equivalent to that of shell 11, base 12A, and teeth 12.

In FIG. 3, the end of shaft 59 is slidably received by aperture 52A formed in member 42A and interlocks with another portion of shaft 59 (not visible) inside member 42A. Members 57 and 58 are not, for sake of clarity, illustrated on shaft 59 in FIG. 3.

Figure 6:
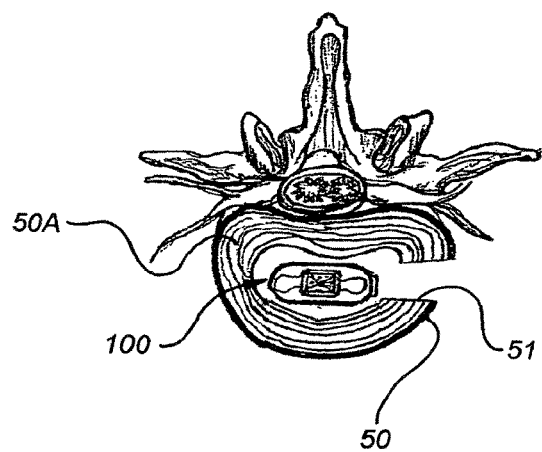
FIGS. 6-7 illustrate various views of intervertebral implants implanted in an intervertebral space between adjacent vertebrae to correct or withdraw a disc herniation, and optionally expanding the vertebrae apart.

FIG. 6 illustrates the insertion of implant device 100 in a disc 50. An opening 51 is formed through the annulus 50A and implant device 100 is inserted inside the annulus 50A. In FIG. 6, the size of the opening 51 is greater than normal and is exaggerated for purposes of illustration, and the opening 51 can be any size, preferably smaller, or a natural herniation opening. When device 100 is inserted in disc 50, teeth 12 are retracted (FIG. 4) in the housing. After device 100 is inserted, the end of a tool 101 (FIG. 1A) is inserted in and engages opening or indent 31A and the tool is used to turn shaft 59 in the direction of arrow A to outwardly displace shells 11 and 11A and to deploy teeth 12. While not shown, the device can include an internal aperture dimensioned for being received over a guidewire. For example, the internal aperture can be through the shaft 59.

Another particular advantage of the invention is that in many cases it is not necessary to make an opening in disc 50 in order to insert device 100. Device 100 preferably has a shape and dimension that permit insertion through a pre-existing rupture in the annulus of a disc 50. The device can be inserted through the rupture "as is" (i.e., as the rupture exists), or the rupture can, if necessary, be widened sufficiently to permit insertion of device 100 through the rupture and annulus into the nucleus area circumscribed by the annulus. When a device 100 is inserted through a pre-existing rupture—either by inserting device 100 through the rupture as is or by widening and increasing the size of the rupture—it is not necessary to form another opening in the disc annulus.

Figure 7:
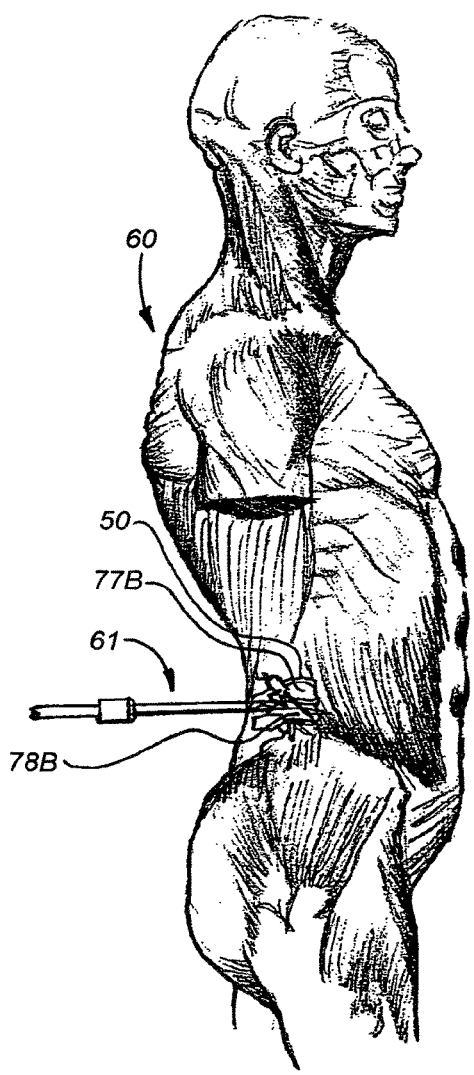

FIG. 7 illustrates a surgical instrument 61 being utilized to insert implant device 100 into an intervertebral disc 50 that is adjacent and intermediate an upper vertebra 77B and a lower vertebra 78B in the spinal column of an individual 60. As would be appreciated by those of skill in the art, individual 60 is normally in a prone position when a device 100 is inserted in a disc 50. One particular advantage of the invention is that in many cases it is not necessary to force apart the vertebrae 77B and 78B bounding a disc 50 in order to insert device 100. Device 100 preferably has a planar shape and dimension that permits an incision to be made in disc 50 (preferably without cutting out a portion of disc 50) and the incision to be widened sufficiently to insert device 100 inside the disc 50. Any desired method can be utilized to insert device 100 in disc 50.

One method for inserting device 100 in the interior of disc 50 in the front, back, or one of the sides without previously or simultaneously separating the pair of vertebrae between which disc 50 is sandwiched. This method may include the step of using a needle to palpate and penetrate the annulus to the center of the disc. The stylette is removed from the needle and a guidewire is inserted until the tip of the wire is in the disc. The needle is removed from the guidewire. A dilator is placed on the guidewire and is used to enlarge the opening in the annulus. The wire is removed. A tube is inserted over the dilator. The dilator is removed. The device 100 is inserted through the tube into disc 50. The tube is removed. Before or after the tube is removed, an appropriately shaped and dimensioned tool 101 (FIG. 1A) can be inserted through the tube (or hole) to engage and turn head 30 to outwardly displace shells 11 and 11A and deploy teeth 12. Alternatively, the guidewire can be retained and used so that the device 100 is slid over the guidewire with or without the tube, and the guidewire can be withdrawn before the tool 101 expands the implant. The teeth 12 can be deployed so that the engaging surface engages the vertebral bone surface or disc material therebetween. Preferably, the engaging surface engages the bone directly, which can allow for the bone to grow to combine with the engaging surface. The bone may grow into and/or around teeth and recesses in the engaging surface. This method can be employed with any of the implants described herein, where a cam can be cammed in order to expand the implant and engage the adjacent vertebral surfaces.

Figure 8:
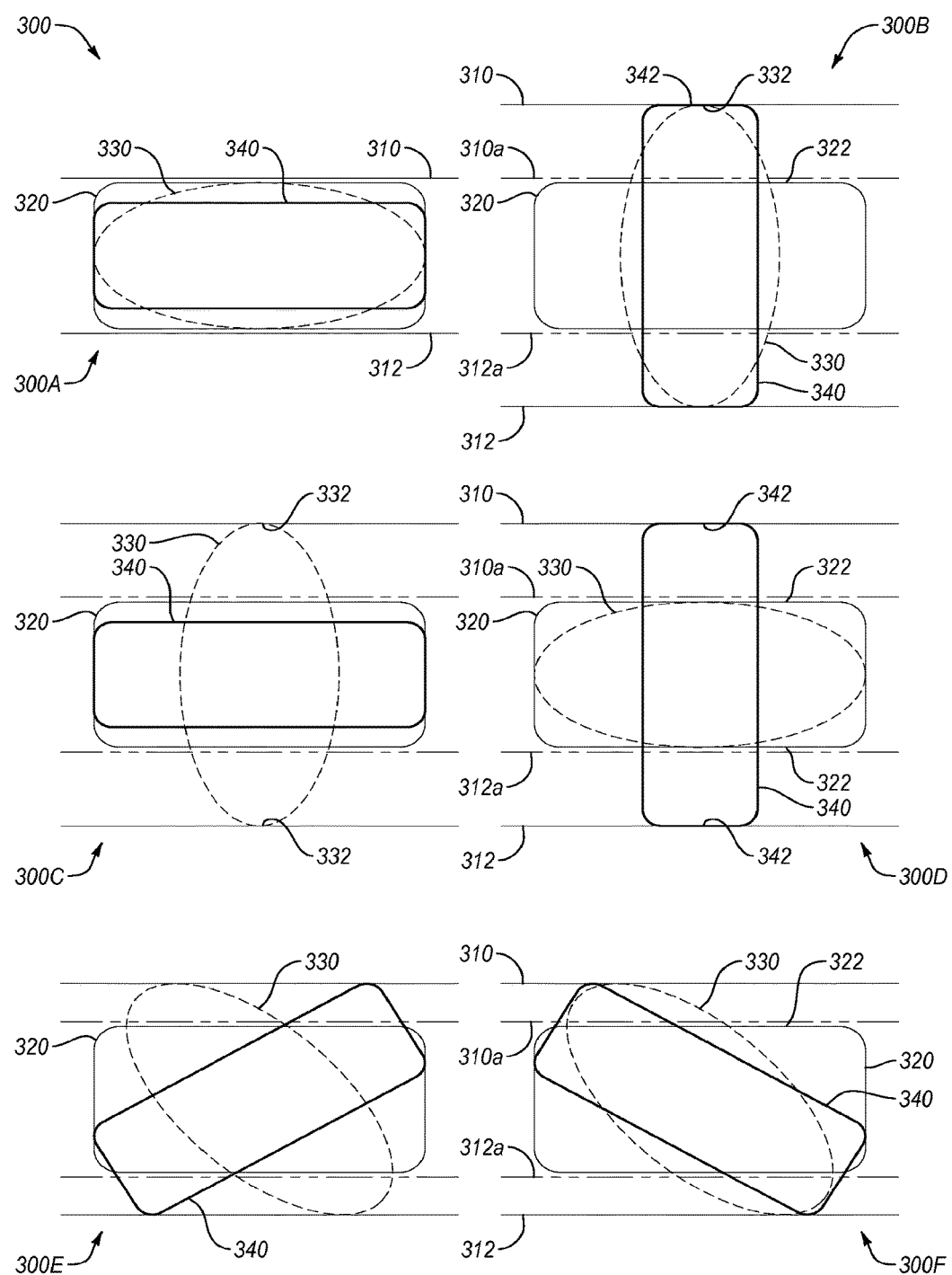
FIG. 8 illustrates longitudinal views of an implant housing, cam, and rotatable plate with respect to two adjacent vertebrae.

Use of a disc revitalization device, such as implant device 100 or any other implant described herein or in an incorporated reference, is further described with reference to FIGS. 8 and 9. In FIG. 8, damaged disc 95 has been compressed between vertebrae 90 and 91 and is bulging outwardly through and from the bottom 92 of vertebra 90 and the top 93 of vertebra 91. The disc 95 has ruptured at two locations and herniated nucleus material 96 and 97 from the nucleus extends outwardly through the ruptures. In FIG. 8, the bulging of disc 95 outside of vertebrae 90 and 91 is, for sake of simplicity, pictured as being uniform around the perimeter of the vertebrae. This is not normally the case. The amount that the disc 95 bulges typically varies with the location on the periphery of the bottom 92 of vertebra 90 and top 93 of vertebra 91. Similarly, the herniation of herniated nucleus material 96 and 97 is, for sake of simplicity, pictured in a generally uniform spherical shape. This is not normally the case. The shape of a herniation of nucleus material need not be uniform or have the shape and dimension of any recognizable symmetric geometric figure.

After device 100 is inserted internally into the nucleus of disc 95, a tool with a driver end is inserted in opening 31A and the tool is utilized to turn head 30 in the direction of arrow A (FIG. 1) to displace and expand shell 11 outwardly in the direction of arrows D and E, to displace and expand shell 11A of FIG. 2 outwardly in the direction of arrows X and Y and away from shell 11 (FIG. 1), to deploy teeth 12 to engage a portion of the bottom 92 of vertebra 90 (FIG. 8), to deploy teeth associated with shell 11A to engage a portion of the top 93 of vertebra 91, and to subject disc 95 to internal traction by displacing vertebrae 90 and/or 91 vertically along axis G in a direction generally normal to the bottom 92 of vertebra 90 and to the top 93 of vertebra 91 to increase the separation distance between vertebrae 90 and 91, to increase the height (H) of disc 95, and to decrease the width (W) of disc 95. Since a spine is generally curved along its length, vertebrae in the spine are not stacked one directly on top of the other along a straight vertical axis. One vertebra usually is slightly canted with respect to its adjacent vertebra. Nonetheless, the axis G can be said to be generally normal (with plus or minus 45 degrees) to the bottom 92 of one vertebra and to the top 93 of an adjacent vertebra.

When disc 95 is subjected to internal traction, the disc 95 often tends to undergo a transformation from the short, squat, bulged configuration of FIG. 8 to the tall, retracted configuration illustrated in FIG. 9. The bulged part of the disc 95 retracts inwardly to a position between vertebrae 90 and 91 in the same general manner that the bulge 105 in rubber band or string 102 (FIG. 10) retracts inwardly when the ends of the string 102 are pulled in the directions indicated by arrows 103 and 104 to produce the "taller" (i.e., longer) string 102 illustrated in FIG. 11. When bulge 105 retracts inwardly, the width W of the disc 95 is reduced.

Further, when disc 95 takes on the tall, retracted configuration of FIG. 9, the volume of the space inside and circumscribed by the inner edge of the annulus (i.e., the space in which material comprising the nucleus is found) increases because the increase in the height of the space concomitant with the increase in the height of disc 95 usually offsets and is greater than the decrease in the diameter or width of the space concomitant with the retraction of the disc 95. The increase in the volume of the space in which the nucleus is found generates negative pressure or generates forces that tend to pull or permit the herniated nucleus material 96 and 97—that prior to internal traction extended outwardly through ruptures in the annulus 94 in the manner illustrated in FIG. 8—to move through the associated disc ruptures and back into the inner annular space in which nucleus material is ordinarily found. Increasing the height of and retracting disc 95 also tends to close or partially close ruptures 98 formed in the annulus 94 (FIG. 9) so that the ruptures 98 often will heal completely closed of their own accord. Similarly, if an opening has been made through the annulus 94 to facilitate insertion of a device 100, the internal traction of disc 95 tends to close the opening to facilitate healing of the opening. Such an incision normally, but not necessarily, would be vertically oriented in the same manner that rupture 98 is vertically oriented in FIG. 9.

The device 100 can be oversized and shaped such that during internal traction the device 100 prevents the internal opening (which opening would be bounded by the internal wall of the annulus) in the annulus of disc 95 from completely retracting or reducing in size to a particular width when a disc moves from the bulging configuration of FIG. 8 to the retracted, taller configuration of FIG. 9. When device 100 prevents the internal opening in the annulus from fully inwardly retracting or constricting along axes that lie in a horizontally oriented plane that is generally normal to axis G in FIG. 9, the annulus and/or nucleus generate and maintain for at least a while compressive forces against the device 100. This "tensioning" of the annulus and/or nucleus tends to anchor the device 100 in position in disc 95, to prevent migration of device 100, and therefore to produce a unitary, stronger structure comprised of the disc 95 and the "captured" or a "squeezed" device 100.

The shape and dimension and constructions of the device 100 can vary as desired provided that device 100, when inserted in a disc 95, can be utilized to separate a pair of adjacent vertebrae 90 and 91 the distance necessary during internal traction to obtain the desired retraction and height increase of a disc 95 intermediate the pair of vertebrae. It is desirable that device 100 functions to contact the nucleus and/or annulus of the disc 95 to produce the desired shape of disc 95, and/or that the device 100 functions to contact the nucleus and/or annulus of the disc 95 to produce tension in the annulus and/or nucleus because the device 100 prevents disc 95 from fully retracting and causes the nucleus and/or annulus to squeeze or compress device 100. While the device 100 has been described for use in the therapeutic methods, the device 200 of FIGS. 12A-12F may also be used.

Figure 12B:
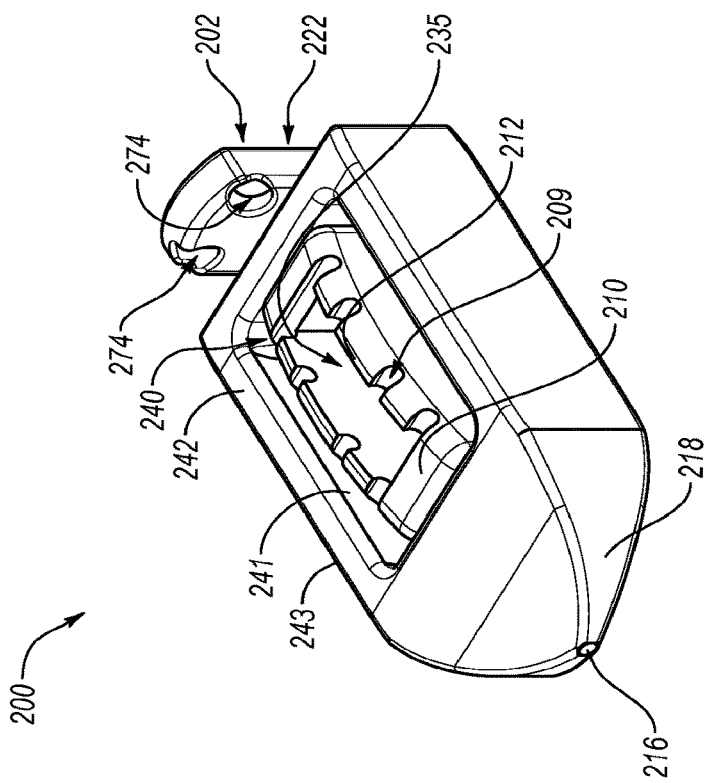
FIG. 12B is a perspective view of the implant of FIG. 12A in a second rotated and cammed position, which deploys engaging surfaces with engaging surfaces.
Figure 12A:
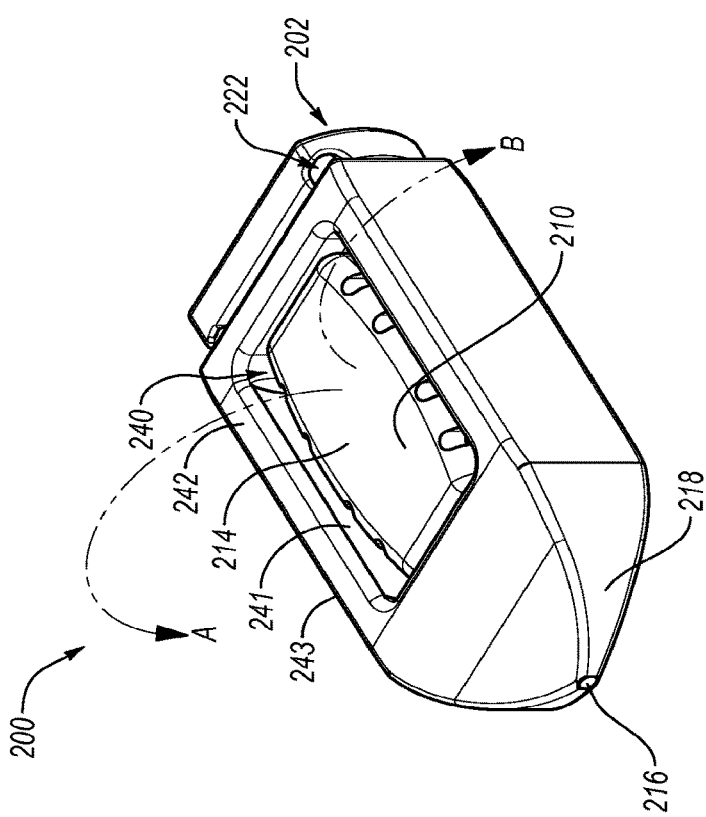
FIG. 12A is a perspective view of an implant illustrating a cam member in a first position (e.g., first housed position or retracted position).
Figure 12C:
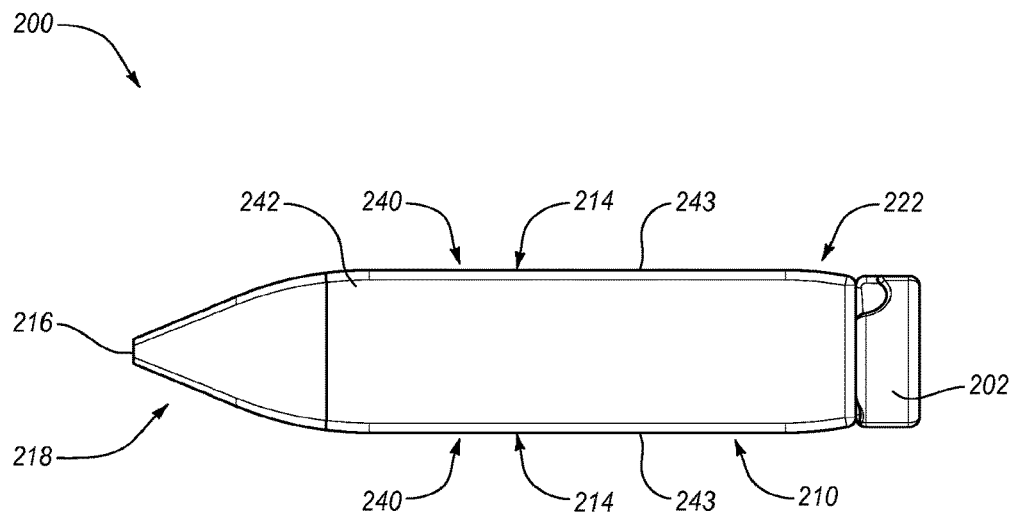
FIG. 12C is a side view of the implant of FIG. 12A in the first position.
Figure 12D:
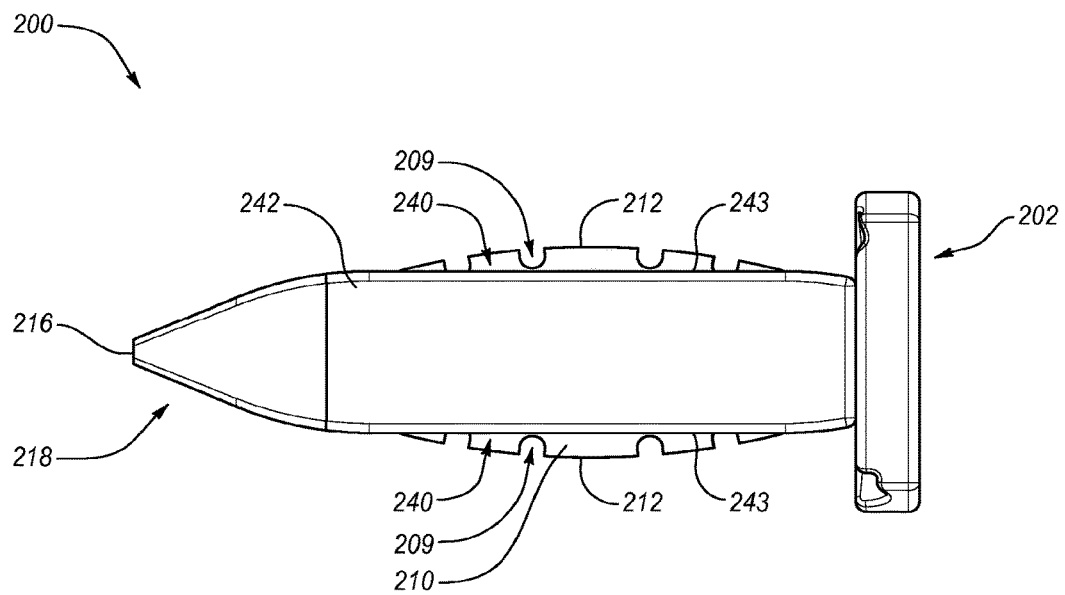
FIG. 12D is a side view of the implant of FIG. 12B in the second rotated and cammed position.
Figure 12E:
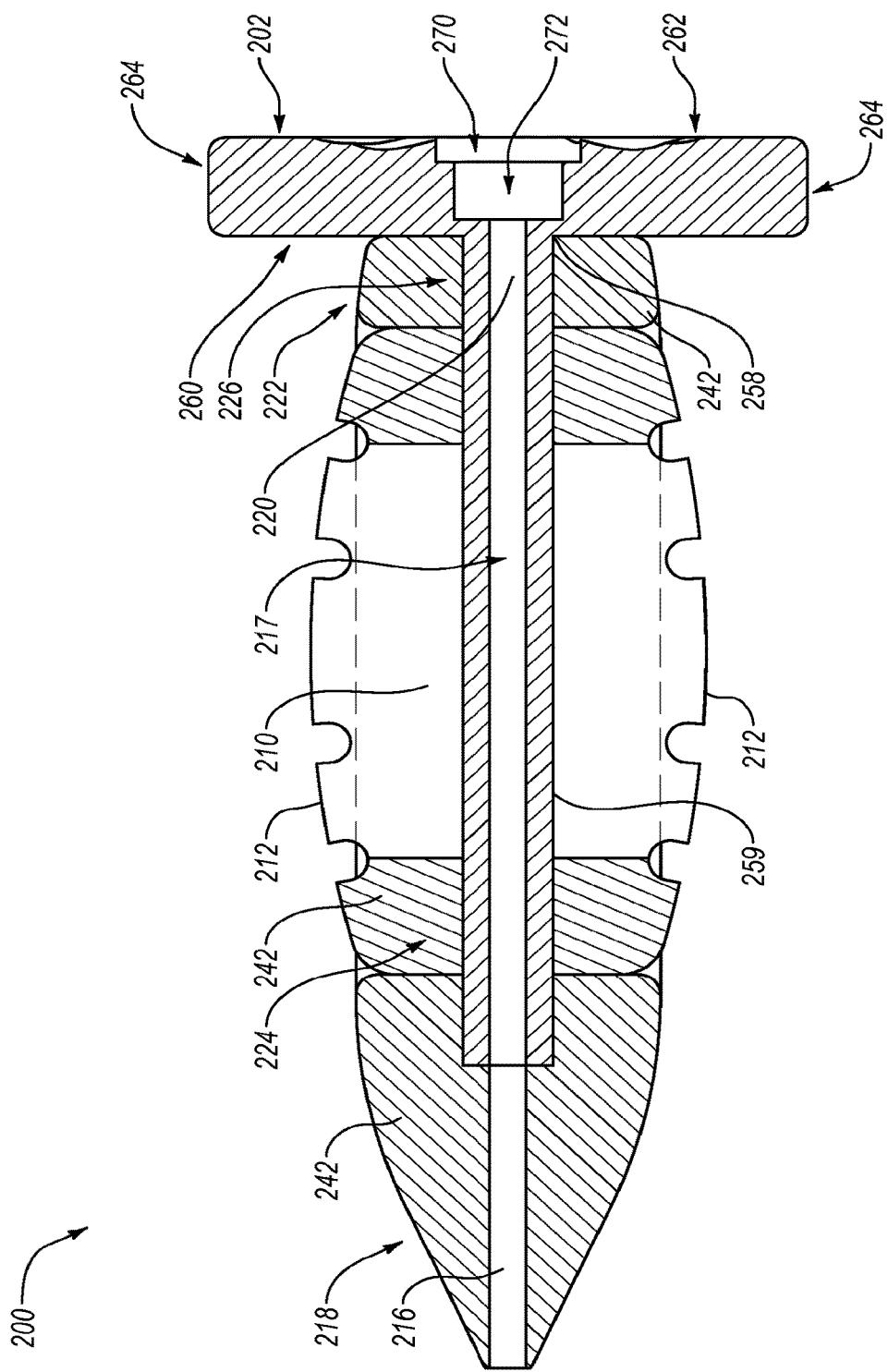
FIG. 12E is a cross-sectional side view of the implant of FIG. 12D in the second rotated and cammed position.

FIGS. 12A-12F demonstrate a device 200 configured to selectively extend engaging surfaces 212 from one of the openings 240 in a housing 242 by rotating from a retracted orientation (FIGS. 12A and 12C) to an extended orientation (FIGS. 12B and 12D). The engaging surfaces 212 can be recessed or protrude past housing surfaces 243 depending on the positioning of rotation. The extended engaging surfaces 212 can engage one or more vertebral surfaces or tissue therebetween in order to press and apply a force or pressure to push the vertebral surfaces away from each other or hold the vertebral surfaces apart at a defined distance. This can be used to improve the functioning of an intervertebral disc positioned between, contacting, and separating a pair of vertebrae in a spine having a longitudinal axis, the disc including an annulus having a height (H) and a width (W). The device can be configured to contact at least one of the pair of vertebrae, separate the pair of vertebrae along the longitudinal axis of the spine, increase the height (H) of the disc, and decrease perpendicularly the width (W) of the damaged disc. The device 200 can be configured to extend the engaging surfaces 212 as described herein, and with regard to turning a cam and camming and substrate 12A lifting of FIGS. 1-5 to push one or both of the opposite engaging surfaces 212 from the opening 240. That is, the cam mechanism of FIGS. 1-5 can be applied to the implant 200. The engaging surfaces 212 can include a cavity 235 or recess defining member that diverges inwardly from the engaging surfaces 212. The cavity 235 can be empty or include a porous member or material, which may include an active agent that promotes bone growth into the cavity 235 or general healing.

The engaging surfaces 212 can include one or more omega recesses 209 ("Ω"). The omega recesses 209 can be short (e.g., hole-like) or elongate (e.g., trough-like), and may extend partially or all the way across the engaging surfaces 212. The omega recesses 209 can allow for bone ingrowth and interlocking of the engaging surfaces 212 and vertebrae. The omega recesses 209 allow for the engaging surfaces 212 to engage with the vertebrae so as to be in fixed locations. The omega recesses 209 may be empty or include a porous member or material, which may include an active agent that promotes bone growth into the omega recesses 209 or general healing.

The device 200 can include a cam member 210 that has engaging surfaces 212 that extend outwards further than retracted surfaces 214 from a cam rotational axis. The cam member 210 is operably coupled with a shaft 259, such that rotation of the shaft 259 rotates the cam member 210 between the retracted surfaces 214 being exposed in the opening 240 (e.g., retracted position) and the engaging surfaces 212 being exposed and protruding from the opening 240 (e.g., protruding position). When in the retracted position, the engaging surfaces 212 face or are oriented towards the walls 241 that define the opening 240. When in the protruding position, the retracted surfaces 214 face or are oriented towards the walls 241 that define the opening 240. While the cam member 210 is shown to include two engaging surfaces 212 and two retracting surfaces 214, more can be included by having 6, 8, 10, or more of such surfaces. Rotating the cam member 210 in the direction of arrows A and B, from a first housed position (e.g., retracted position) to a second deployed position (e.g., protruding position) rotatably deploys the engaging surfaces 212.

Figure 13A:
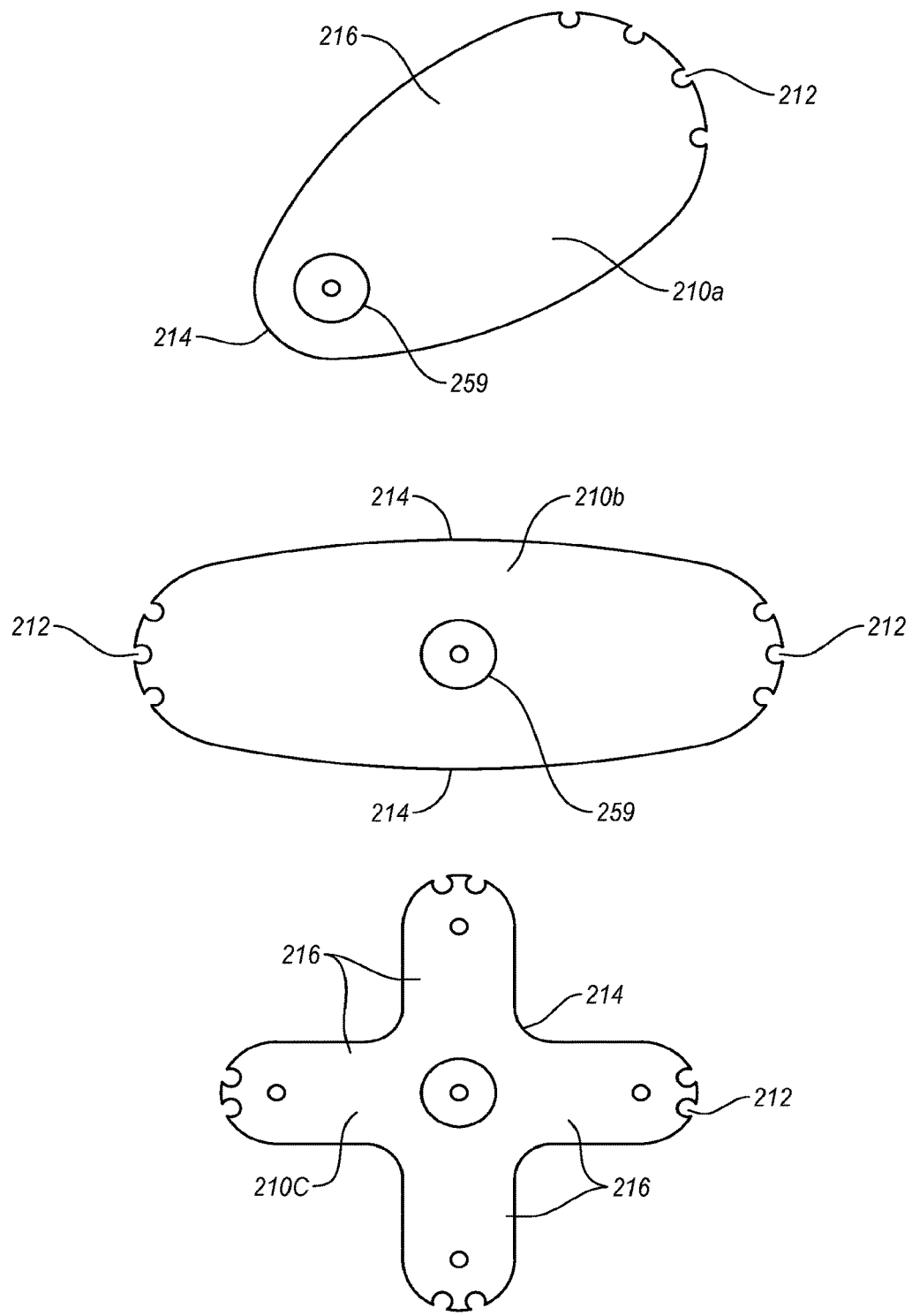
FIG. 13A provides side views of different embodiments of cams for the implant.

The cam member 210 (don't see this on 13A) can be configured with various different cross-sectional profiles that can cam one or more camming surfaces to protrude further away from a cam rotational axis of the cam compared to the non-camming surfaces, which can be seen in FIG. 13A.

The housing 242 can include a first longitudinal aperture 216 extending from first end 218 to the wall 241 defining the surface of the opening 240 and a corresponding or aligned second longitudinal aperture 220 extending from a second end 222 to the wall 241 defining the surface of the opening 240. In order to allow the device 200 to be delivered by a guidewire, the shaft 259 and/or cam 210 can include a guidewire aperture 217 extending from a first cam end 224 oriented at the first end 218 of the housing 242 and a second cam end 226 oriented at the second end 222 of the housing 242. The guidewire aperture 217 stays aligned with the first longitudinal aperture 216 and second longitudinal aperture 220, which can be on a longitudinal axis of the device 200, housing 242, cam 210, and shaft 259, which can be the cam rotational axis.

The first end 218 of the housing 242 can be tapered from the wall 241 of the opening to the first longitudinal aperture 216. The middle portion of the housing 242 can include a rectangular cross-sectional profile from the first end 218 to the second end 222. The opening 240 can also have a rectangular cross-sectional profile in order to house the engaging surfaces 212 when retracted. The second end 222 can be blunt compared to the tapered end. However, the first or second ends can be any shape ranging from pointed, tapered, sloped, rounded, concave, convex, flat, or a combination thereof. The flat second end 222 is configured to accommodate a rotatable plate 202. However, the rotatable plate 202 can be optional. Also, the housing 242 can include one or more fastener apertures that extend from the second end 222 at an angle through the top side and/or bottom side of the housing 242. For example, one fastener aperture can extend from the second end 222 through the top surface and second fastener aperture can extend from the second end 222 through the bottom surface.

The plate 202 can include a body having a first side 260 that faces the housing 242 and includes a portion that is connected to the shaft 259 at end 258. The plate 202 connects to the shaft 259 and to the cam 210, and thereby rotating the plate 202 can rotate the cam 210 from a retracted position to a protruding position through opening 240 in the housing 242. The coupling between the plate 202 and the shaft 259 can be threaded, snap-fit, friction fit, integrated, permanent, or removable. The coupling can be via screw, weld, adhesive, snap-fit, or other coupling mechanism. The coupling is sufficient such that when the plate 202 rotates, the shaft 259 rotates the cam 210. However, the plate 202 can be configured to rotate relative to the housing 242 without rotating the shaft 259, and thereby the plate 202 can rotate independently of the cam 210 and/or shaft 259.

The plate 202 also includes an opposite second side 262 and ends 264 with a rectangular cross-sectional profile. The lengths of the first side 260, second side 262, and ends 264 can be modified or tailed as needed or desired. The plate 202 can have an aligned orientation where the rectangular cross-sectional profiles of the housing 242 and plate 202 align, or staggered orientation where the rectangular cross-sectional profiles form a cross or plus sign ("+"), or staggered in any orientation between aligned and orthogonal. The ends 264 can be between the housing surfaces 243 in the aligned orientation and protrude past the housing surfaces 243 in the staggered orientation. The aligned and staggered orientations of the plate 202 may or may not correspond with the recessed and protruding positions of the cam 210, where aligned would be recessed and protruding would be staggered. The plate 202 can have one or more apertures extending from the first side 260 to second side 254, which apertures may be orthogonal with the first side 260 and second side 264 or at an angle therewith, usually up to 45 degrees, but higher-degree angles may be useful. These apertures can be fastener apertures with fastener threading.

In one embodiment, the first end 218 of the housing 242 is tapered and has first longitudinal aperture 216 formed in the housing 242 and that is aligned with a guidewire aperture 217 that extends along or through shaft 259 and aligned with second longitudinal aperture 220 in the second end of the housing 242 to allow device 200 to be slid along a guidewire or other guidance member for implantation. That is, a first longitudinal aperture 216 effectively extends from the tip of the housing 240 to the plate 202.

The shaft 259 can be molded, screwed, ratcheted, integrated, or otherwise combined to the cam 210. The shaft 259 can be mounted to the plate 202 by being rotatably or fixed therewith. The shaft 259 can protrude through a shaft aperture 270 in the plate 202 so that an end having a fastener receiver can be exposed for rotation by the fastener. The shaft 259 may also be integrated with the plate 202 so that rotation of the plate rotates the shaft 259. As such, the shaft 259 and plate 202 can rotate together or separately.

Figure 12F:
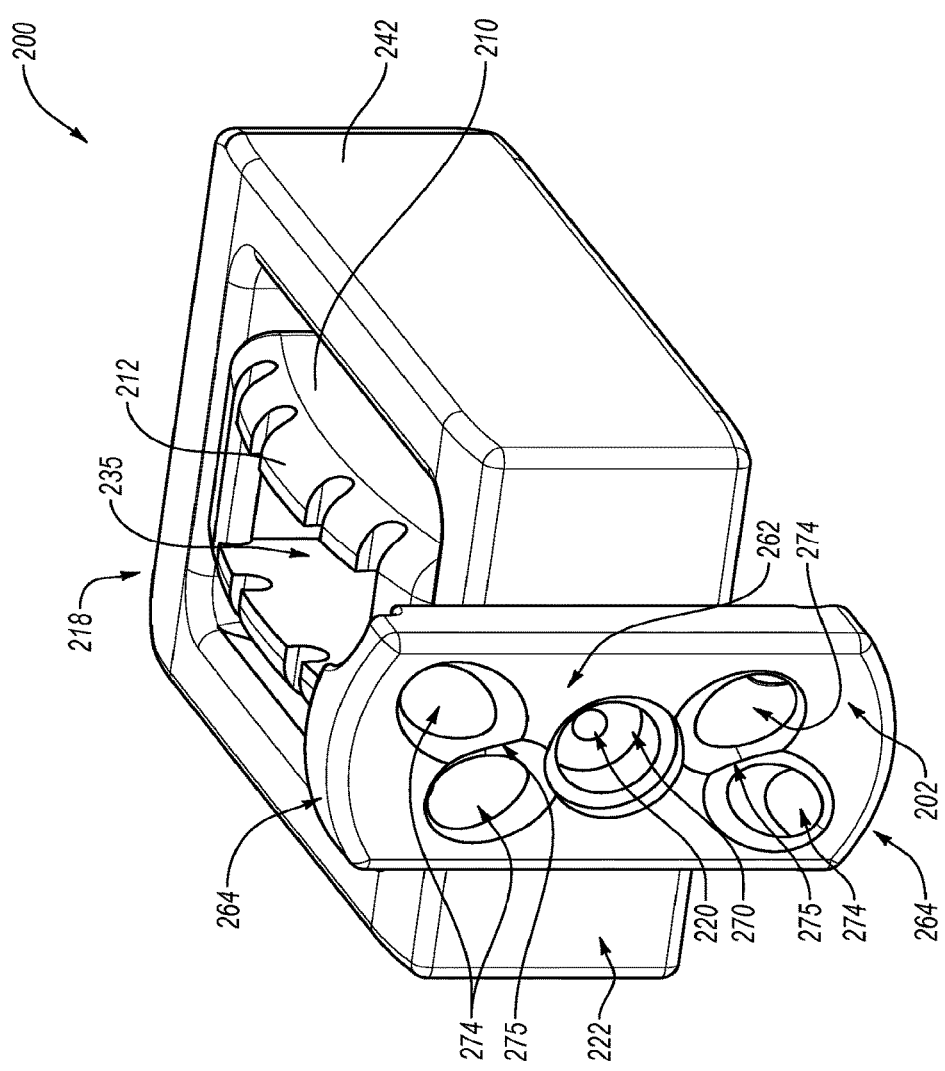
FIG. 12F is a back perspective view of the implant of FIG. 12D in the second rotated and cammed position.

FIG. 12F shows the second side 262 of the plate 202 and second end 222 of the housing 242. The plate 202 can include a body that has a guidewire aperture 270 or a shaft aperture 270 extending all the way therethrough. The plate 202 can also include one or more bone fastener apertures 274 that can extend from the first side 260 to second side 262 orthogonal or angled therewith. The fastener apertures 274 are shown to be between center axis and the ends 264, and at the same orientation or have angles with respect to each other. The fastener apertures 274 can be configured for a locking set screw (not shown). Locking screws can be inserted through fastener apertures 274 and can interfere with each other at interface 275, by the second installed locking screw protruding past a more recessed first installed locking screw. The fastener apertures 274 can be oriented in the plate 202 so that the fasteners can be received into adjacent vertebrae without passing through the housing 242 when the plate 202 is staggered or orthogonal from the housing 242.

Figure 12G:
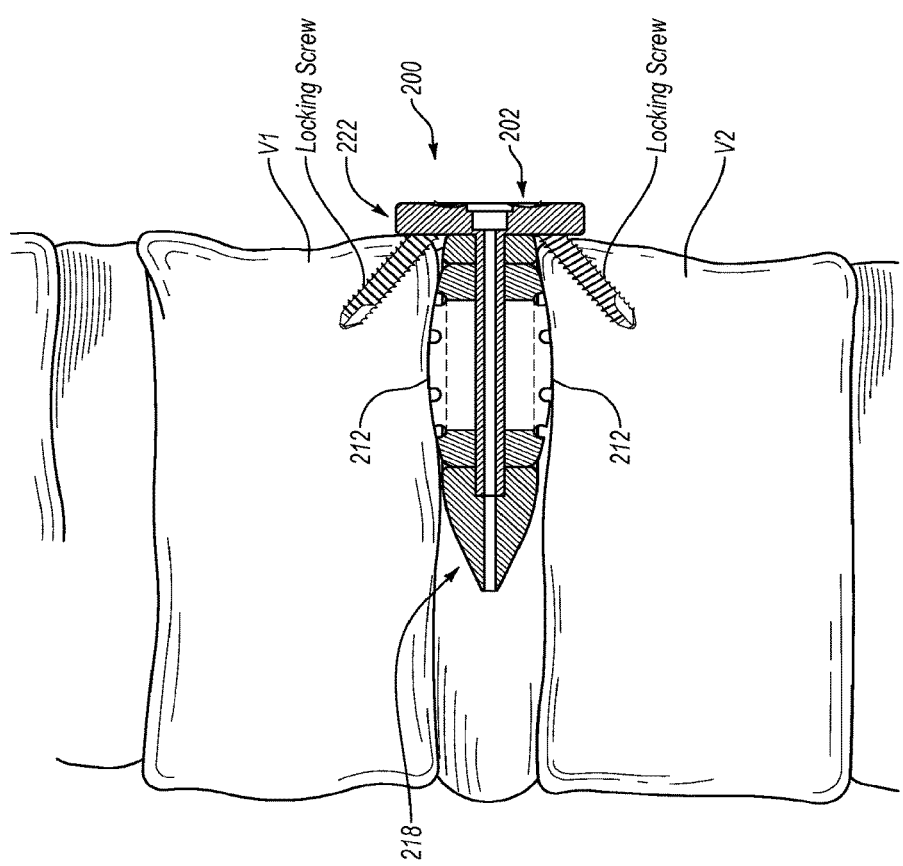
FIG. 12G is a side view that illustrates implantation of the implant between two adjacent vertebrae.

FIG. 12G shows the device 200 inserted into a disc space between adjacent vertebrae V1 and V2. The device 200 includes the plate 202 perpendicular to the housing 242 so that the cam 210 is deployed and can contact the vertebrae V1 and/or V2. While not shown, locking screws can be inserted through the apertures 274 and into the vertebrae V1 and V2. Rotating the cam 210 from the recessed position to the protruding position allows for the two engaging surfaces 212 to engage both vertebrae V1 and V2, which can either hold the vertebrae V1 and V2 a set distance apart or actually push the vertebrae V1 and V2 away from each other.

The plate 202 can be integrated with the shaft 259 so as to be configured to rotate the cam 210. Rotating plate 202 provides increased leverage for the cam 210 and is therefore an improved method of internal traction which functions to separate adjacent vertebrae and change the shape and dimension of the intervertebral disc. Rotating plate 202 to rotate the cam 210 also is an improved method to change the alignment of the adjacent vertebrae. The plate 202 may also function as a cam to separate the adjacent vertebrae when located and rotated therebetween.

Additionally, the cam 210 can include a cavity 235 configured as a recess or aperture. The cavity 235 can extend inwardly from the engaging surfaces 212 toward the guidewire aperture 217. The cavity 235 can be any dimension so long as there is sufficient engaging surfaces 212 to engage the vertebrae described herein. The cavity 235 may be omega shaped (e.g., "Ω"), but may be larger than the other omega recesses 209 and may be oriented at an angle therefrom, such as orthogonal. The cavity 235 can be of any depth. The cavity 235 can be empty to allow bone ingrowth or filled with a filler material. Often, the filler material is different from the cam material. The cavity 235 can be filled with a porous material or other material such as bone graft, disc, porous metal, polymers, therapeutic agents, tissue scaffolds, and the like. Rotating cam 210 to the protruding position exposes cavity 235, which allows for the filler material to contact or be adjacent to a vertebra surface. This orientation allows for the cam 210 to deliver the filler material to be adjacent to the vertebra for promoting fusion, interlocking, or other association of the vertebra bone with the engaging surface. Accordingly, the device 200 can function as a containment shuttle for delivering materials to the disc space and/or vertebrae. The material can be placed in cavity 235 when in the exposed orientation, and then the cam 210 can be rotated to the retracted position to contain the material during the implantation procedure. Then the cam 210 is rotated to expose the material in the cavity 235 to the vertebrae and/or disc space. The cavity 235 described herein can contain a shelf, ridge, ratchet, protuberance, or omega shape ("Ω") or the like to retain the materials and to interlock with bone ingrowth. While the cavity 235 can be omega shaped, it may also be "C" shaped or "U" shaped. The cavity 235 can be elongate from one end of the cam 210 to the other, the cavity can have any shape or size, and a plurality of cavities 235 can be included in the engaging surfaces 212. The cavity 235 can intersect with one or more of the omega recesses 209. In one preferred embodiment, cavity 235 has a ridge that prevents a porous material (e.g., metal, bone) from displacing or falling out of the cavity 235 once press fit into the cavity 235.

In one embodiment, a method of separating adjacent vertebrae can include rotating the cam of the implant from a first housed position (e.g., retracted position) to at least a second deployed position (e.g., protruding position) so as to rotatably or arcuately deploy an engaging surface and press the engaging surface against bone. This can include pressing a material in the cavity against the bone or disc. A method of removal of the implant can include rotating the cam from the protruding position to the retracted position and withdrawing the implant from between the adjacent vertebrae. In one embodiment, separating the vertebrae generates negative pressure sufficient to change the shape of the disc, such as withdrawing a bulge or herniation.

In another embodiment, the side of a plate can have tabs, teeth, or protuberances for interlocking or ratcheting with the housing as the plate is rotated and vice versa. Similarly, the housing can have tabs, teeth, or protuberances for interlocking or ratcheting with recesses in the shaft and/or cam, and vice versa.

The implant device can be configured to include a rotatable element that is configured to turn a cam. The cam is operably coupled with at least one interlocking tooth or recess of an engaging surface. The cam can be shaped and dimensioned to separate adjacent vertebra when the cam is cammed against the vertebra. The cam can be integrated with the rotatable element or can include a ribbed tooth element that interlocks with at least one slot on the other member, or vice versa. The engaging surface can be configured to move unidirectionally, multidirectionally, rotationally, or poly-axially. The cam can be rotated from a first housed position to at least a second deployed position, which can arcuately deploy retractable bone-engaging teeth and/or recesses of the engaging surface. The cam can be rotated so as to separate the vertebrae and generate negative pressure sufficient to change the shape of the disc. Rotating the cam from a first housed position to at least a second deployed position can expose a porous material with or without beneficial agent to the bone surfaces of the vertebrae. The beneficial agent can promote bone ingrowth into the porous material. The rotatable element can be a plate, bolt, screw, shaft, or the like.

The implant device can include a cam; a rotatable plate configured to rotate the cam; one or more interlocking teeth members operably coupled with the cam; and one or more ribbed teeth interlocked with one or more corresponding slots on a base of a substrate having the interlocking teeth members operably coupled with the cam, where the base is configured to move unidirectionally, multidirectionally, rotationally, and/or poly-axially with respect to cam. The implant device has a first housed position with the one or more interlocking teeth members not exposed from the housing and a second deployed position with the one or more interlocking teeth exposed from the housing.

The implant can be used to manipulate and revitalize a spinal column disc while minimizing or preventing the removal of material comprising the disc. The implant can be inserted in the disc either through a pre-existing rupture or through an opening formed in the front, back, or sides of the disc. Increasing the space between the vertebrae bounding the disc or removing disc material often is not necessary to insert the implant device in the disc. The implant device generates internal traction or other forces acting on the disc to alter the shape of the disc. The shape of the disc is altered to relieve pressure on nerves adjacent the disc. The shape of the disc is also altered to draw nuclear hernias back into the interior of the disc and to produce a disc shape that improves functioning of the disc.

FIG. 13A shows different views of different cam bodies that can be included in the housing of the implant. The different cam bodies 210*a-c* can have different shapes, have different camming surfaces 212 (e.g., engaging surfaces) at different locations and orientations relative to a cam rotational axis or shaft 259. The camming surfaces 212 can be opposite or otherwise oriented apart from uncamming surface 214 (e.g., retracted surfaces). The camming surfaces 212 can be on cam lobes 216.

Figure 13B:
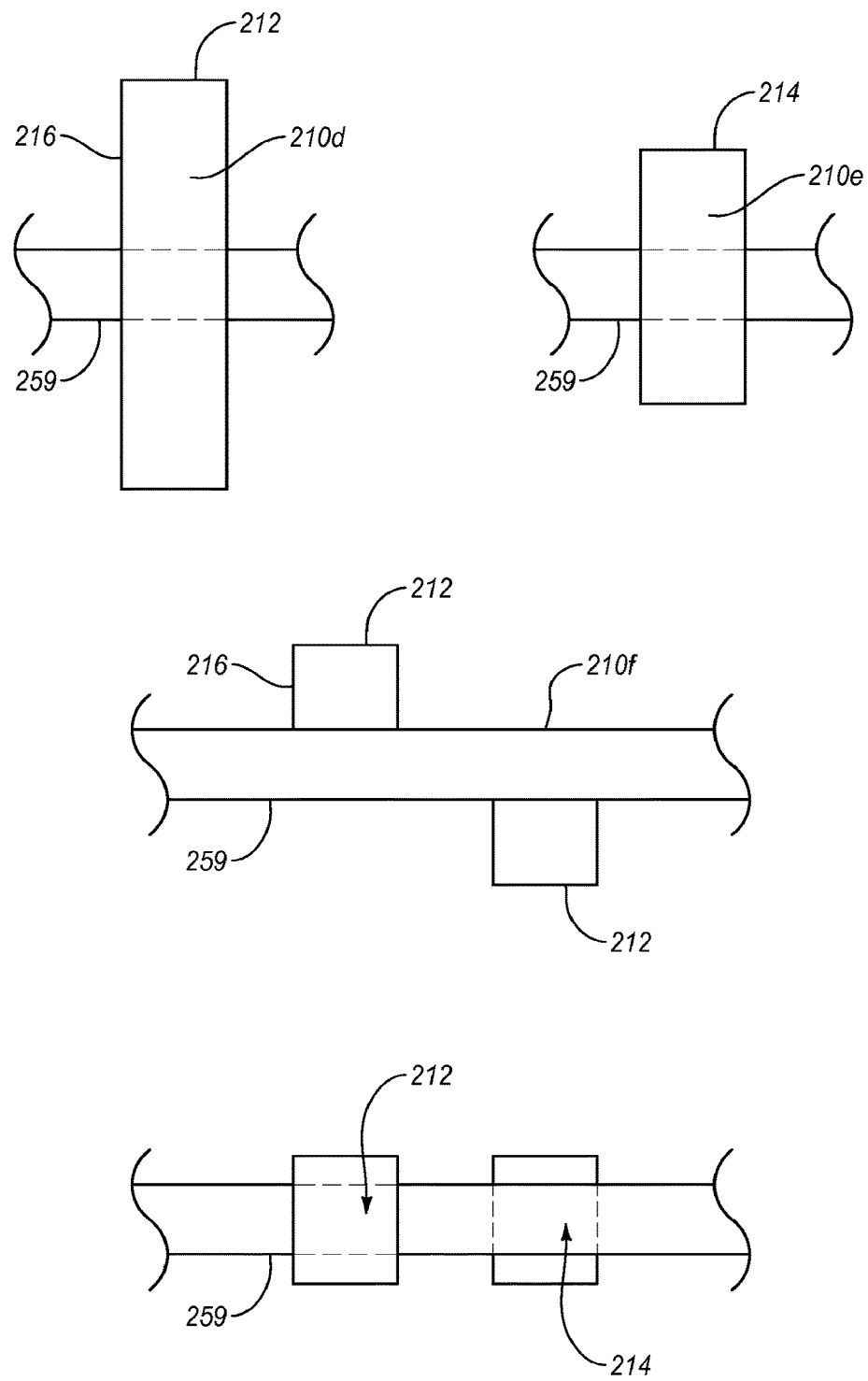
FIG. 13B provides side views of different embodiments of cams and cam shafts for the implant.
Figure 14:
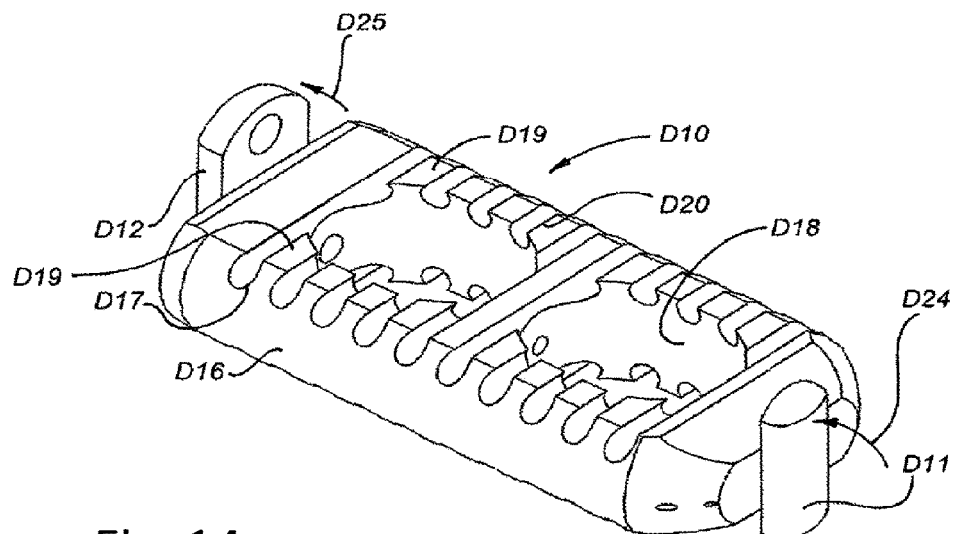
FIG. 14 provides a perspective view of an embodiment of an implant having a cam.
Figure 15:
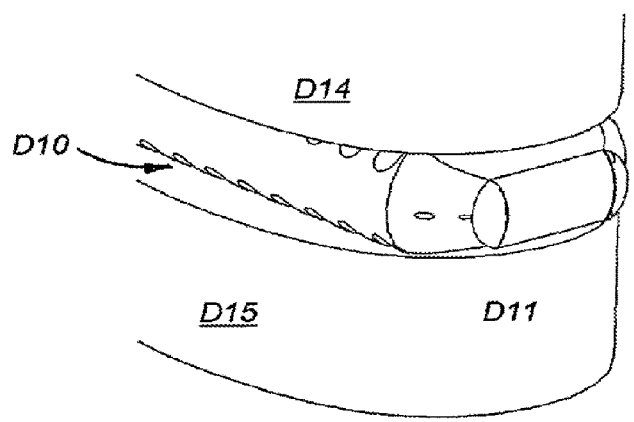
FIG. 15 provides a perspective view of the implant of FIG. 14 being implanted with the cam retracted.
Figure 16:
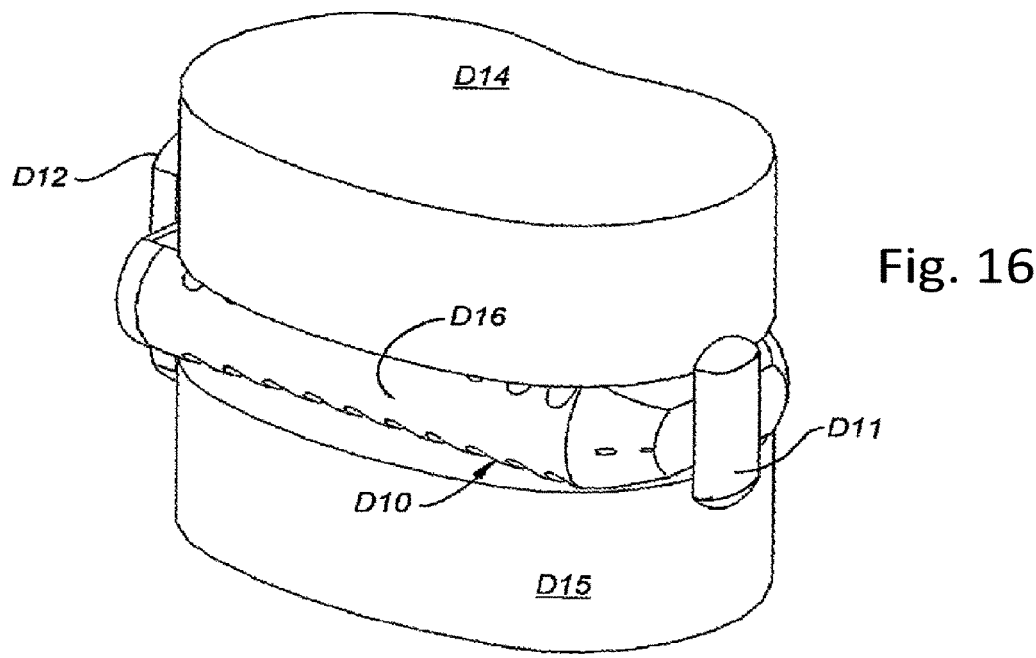
FIG. 16 provides a perspective view of the implant of FIG. 14 being implanted with the cam extended.
Figure 17:
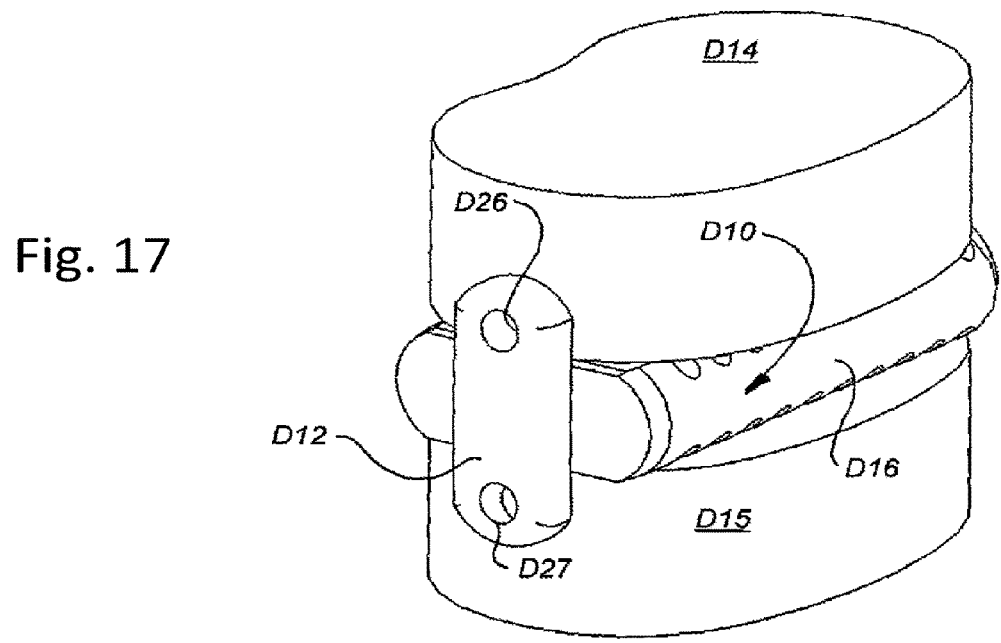
FIG. 17 provides another perspective view of the implant of FIG. 14 being implanted with the wing extended.

FIG. 13B shows different views of a shaft 259 having one or more cam bodies 210*d-g*. The camming surfaces 212 can be protruded further away from the shaft 259 when cammed (e.g., 210*d*, and 2100, and the un-cammed surfaces 214 can be protruded away from the shaft 259 when uncammed (e.g., 210*e* and 210*g*). Or, the camming surfaces 212 can be uncammed (e.g., 210*e* and 210*g*).

FIG. 8 includes a series 300 of embodiments of relative positions of opposite vertebral surfaces 310 and 312 with respect to an intervertebral device having a housing 320, an internal cam 330 (e.g., within aperture cavity) and an external cam 340 (e.g., rotatable plate). The implant can have the housing 320 operably coupled with the internal cam 330 and/or operably coupled with the external cam 340. The implant can be devoid of one of the internal cam 330 or external cam 340, but always has the housing 320 at one cam. The housing 320 can include engagement surfaces 322 (e.g., having engagement members) that contact the vertebral surfaces 310 and 312 when the implant is in a retracted orientation as shown in frame 300A. The internal cam 330 can include the engagement surfaces 322 (e.g., having engagement members) that contact the vertebral surfaces 310 and 312 as shown in frames 300B, C, E, and F. The external cam 340 can include engagement surfaces 322 (e.g., having engagement members) that contact the vertebral surfaces 310 and 312 as shown in frames 300B, D, E, and F. The internal cam 330 is shown to expand the vertebral surfaces 310 and 320 by camming action in frames 300B, C, E, and F. The external cam 340 is shown to expand the vertebral surfaces 310 and 320 by camming action in frames 300B, D, E, and F.

Additionally, FIG. 8 can illustrate a series 300 of embodiments when the vertebral surfaces 310*a* and 312*a* are not separated further by the cam action, such that the vertebral surfaces 310*a* and 312*a* are maintained on the engagement surfaces 322 of the housing 320 in frames 300B-300F, where the internal cam 330 and/or external cam 340 become embedded into the vertebral surfaces 310*a* and 312*a* to a depth of 310 and 312, respectively. Frames 300B and 300D show the external cam 340 to be at 90 degrees from the housing 320 and frames 300B and 300C show the internal cam 330 to be at 90 degrees from the housing 320, which shows maximum camming. Frames 300E and 300F show intermediate angle of camming with the internal cam 330 and external cam 340 both having angles with respect to the housing 320. Accordingly, either the internal cam 330 or external cam 340 or both can be contacting, engaging, and/or embedded in or otherwise coupled with the vertebral surfaces 310 and 312 or 310*a* and 312*a*.

In one embodiment, an intervertebral implant can include: a housing having at least one opening; and a cam mechanism located in the housing; and at least one engaging surface operably coupled with the cam mechanism that is deployable through the at least one opening by rotation of the cam.

In one embodiment, the intervertebral implant can include the intervertebral housing having a first end and second end with a top side and bottom side therebetween, with at least one engagement opening in at least one of the top side or bottom side, the implant having a first dimension from the top side to the bottom side; a shaft rotatably located within the housing and having a shaft head exposed through an end opening in one of the first end or second end, the shaft head having a tool coupling member; the cam mechanism operably coupled with the shaft such that rotation of the shaft rotates the cam mechanism; and the at least one engaging surface operably coupled to the cam mechanism such that rotation of the shaft protrudes and/or retracts the at least one engaging surface through the at least one engagement opening, wherein when the at least one engaging surface protrudes through the at least one engagement opening the implant has a second dimension that is greater than the first dimension. In one aspect, the at least one engaging surface has at least one engaging member. In one aspect, the at least one engaging member includes at least one engaging tooth that penetrates into the disc tissue or vertebral bone and at least one engaging recess that receives disc tissue or vertebral bone therein. In one aspect, the cam mechanism includes a cam body having a rib or slot and a cammed body that is cammed by the cam includes the other of the rib or slot such that the rib and slot slidably mate and cam by rotation. In one aspect, each engaging recess has an opening with a smaller cross-sectional profile that expands to a larger cross-sectional profile within the engaging recess. In one aspect, the housing having at least one engagement opening in the top side and at least one engagement opening in the bottom side, and the cam mechanism is operably coupled to a top engaging surface associated with the top side engagement opening and a bottom engaging surface associated with a bottom side engagement opening.

In one embodiment, the intervertebral implant can have a retracted position having the cam in a first position and the at least one engaging surface retracted into the engagement opening; and a protruding position having the cam in a second position and the at least one engaging surface protruding from the engagement opening. As such, a rotational camming action can deploy or retract the engaging surfaces from the engagement openings and/or with respect to the top or bottom surfaces. In one aspect, the first position is about 90 degrees rotation from the second position.

In one embodiment, the housing end opening can be in a plane that is about 90 degrees from the at least one engagement opening. In one option, the housing can have two engagement openings that are openings for an aperture extending from the top surface to the bottom surface. The two engagement surfaces can each have: a retracted position having the cam in a first position and the engaging surface retracted into the engagement opening; and a protruding position having the cam in a second position and the engaging surface protruding from the engagement opening.

In one embodiment, a cam body of the cam mechanism is integrated with the shaft, the cam body having two opposite cam lobes with opposite engagement surfaces thereon, the cam body being located within an aperture having a top engagement opening in the top surface and a bottom engagement opening in the bottom surface, the cam aperture containing the cam mechanism when in a retracted position having the cam in a first position and the engaging surfaces retracted into the engagement openings, and the cam mechanism having a protruding position having the cam in a second position, and the engaging surfaces protruding from the engagement openings. In one aspect, a cam body of the cam mechanism is integrated with the at least one engagement surface thereon. In one aspect, each engagement surface is on a cammed surface that is cammed by rotation of the cam. In one aspect, the engagement surface is on a furthest perimeter location on the cam body. In one aspect, at least one of the top surface and bottom surface includes at least one engaging tooth that penetrates into the disc tissue or bone and/or at least one engaging recess that receives disc tissue or vertebral bone therein.

In one embodiment, the cam mechanism includes a cam body that has a first cam body lobe and an opposite second cam body lobe and cam rotational axis therebetween, the first cam body lobe having a first engagement surface, the second cam body lobe having a second engagement surface, each engagement surface being on a perimeter of the cam body furthest from the cam rotational axis. In one aspect, the body includes fastener receiving surfaces. In one aspect, the fastener receiving surfaces are in fastener receiving apertures.

In one embodiment, the implant can include a rotatable plate having a first surface rotatably coupled to the end of the housing having the end opening. The rotatable plate can have an aperture having the shaft head therein so that the tool coupling member is exposed through a second surface of the rotatable plate that is opposite of the first surface. The rotatable plate can have a plurality of fastener apertures configured for receiving fasteners therethrough. In one aspect, the rotatable plate has a top surface and opposite bottom surface with a distance therebetween that is the same or smaller than the first dimension. Also, the rotatable plate can include a first side surface (e.g., end of plate) and opposite second side surface (e.g., opposite end of plate) with a distance therebetween that is larger than the first dimension. In one aspect, the rotatable plate is fixed with the shaft such that rotation of the shaft rotates the cam and rotatable plate by the same rotation; however, the plate may rotate with respect to the shaft and/or implant housing.

In one embodiment, a method of implanting an intervertebral implant between adjacent vertebrae can include: inserting the implant having a cam into an intervertebral space between adjacent vertebrae; and rotating the cam from a retracted position to a protruding position so that the at least one engaging surface engages at least one of the adjacent vertebrae. The method can include rotating the cam so as to separate the adjacent vertebrae. The method can include fastening the implant to the adjacent vertebrae with a fastener for each vertebra. These steps may be implemented independently or along with other method steps for implant implantation and vertebral stabilization and separation.

In one embodiment, the rotatable plate (e.g., plate 202) can be configured as a bone plate. The bone plate can be configured as in the incorporated references, such as in the provisional application, where the bone plate has flexible tabs and apertures associated and/or at least partially defined by the flexible tabs. The plate can be a spinal plate embodiment, can be used for stabilizing one or more vertebrae, and can be mounted to a single vertebra or two or more adjacent vertebrae in order to stabilize and facilitate healing of fractures, disc herniations, fusions, inhibition of fusions, and other common spinal plate uses. In some instances, spinal plates can be referred to as lumbar plates, anterior lumbar plates, or lateral plates. The rotatable plate may mount on an outside perimeter surface. However, the rotatable plate may be rotated to be embedded between the vertebrae so as to contact each vertebral surface. Also, the plates can be used to treat spinal deformities, trauma, degenerative lumbar, or the like for treatment of cervical spine applications, anterior column support, posterior applications, or any other. The plates can be used for attachment to one vertebra or to two or more adjacent vertebrae.

The rotatable plates generally are flat or planar structures with various lengths and widths with a thickness that is usually thinner than the length or width. The thinner thickness allows the rotatable plate to fit on or in a bone with a low profile so that the body of the bone plate does not extend too far from the surface of the bone. The rotatable plate can include apertures that are configured to receive screws therethrough for affixation to a bone surface. The apertures can be of various sizes, cross-sectional profiles, and configurations (e.g., threaded or smooth) to receive various types of fasteners, such as bone screws. An embodiment of the invention provides the implant having a rotatable plate configured for attachment to a vertebra. The rotatable plate can be shaped as an oval, rectangle, or other elongated polygon. In one embodiment, the bone plate implant includes at least aperture configured for receiving a fastener therethrough so as to fasten the implant to bone. The aperture can be located on any portion of the body, such as in a main body region or arm body region.

The body, cam, rotatable plate, or engagement members of the implant can be prepared from one or more materials that are biocompatible. The different components can be prepared from different types of materials or all from the same type of material. Examples of materials can include polymers, ceramics, composites, metals, alloys, hybrid materials, and combinations thereof, which can be biostable, biodegradable, or resorbable. The materials of the cams and main housing body can be the same or different.

The implant or components such as the implant body, cam, rotatable plate, or engagement members shown in the figures can include a height, a length, and a width, which can be varied as desired. Also, the cam and plate can each have a height, a length, and a width that are normally less than height, length, and width of the implant body. The shape and dimension of the recesses, apertures, grooves, and slotted grooves can vary as desired.

In one embodiment, a kit can include the implant with the cam and/or rotatable plate as described herein along with one or more fasteners, the fasteners being adapted to be received into the apertures in the housing or rotatable plate. The implant housing, fasteners, cams, and/or other components can be prepared from the same or different biocompatible materials, such as metals, ceramics, polymers, or others.

In one embodiment, the implant and fastener screw can have one or more teeth, protuberances and/or recesses to interlock or reversibly interlock with the implant with the vertebra or screw as desired. That is, the surfaces thereof can include cooperative features that can be received into each other and interlocked. The surfaces can be configured as any of the surfaces of any of the implants in any of the incorporated documents.

In one embodiment, the top and/or bottom surface of the housing of the implant can include recesses, such as a bone-contacting surface, having recesses that can receive bone growth therein. The recesses can be narrower at the opening than the base, or wider at the opening than the base, or have a uniform cross-sectional profile. These bone-receiving recesses can function to lock the implant to bone when bone grows therein. Also, the recesses can be filed with polymers or other compositions that can contain bone growth factors or other active agents to promote bone growth into the bone-receiving recesses.

Fixing the rotatable plate to a vertebra can prevent the rotatable plate, cam, or implant coupled thereto from moving. When the rotatable plate is coupled to an implant housing, once the implant device is rotated, expanded, separated, joined, articulated, pivoted, or otherwise manipulated, the rotatable plate can be attached to bone to inhibit the implant from being further rotated, expanded, separated, joined, articulated, pivoted, or otherwise manipulated.

In one embodiment, the implant with the cam and rotatable plate can be configured similar to the implant of FIGS. 197, 198, 288-291, 310-311, 320-323, and 330-335 of the incorporated references, such as U.S. patent application Ser. No. 13/605,756.

The implants, housing, cams, and rotatable plate can be made out of stainless steel or another metal. The material used to make implant, housing, cam, and rotatable plate can vary as desired, and include elastic or resilient or other materials. There are, for example, polymers available that produce a rigid, hard implant generally comparable to that produced by stainless steel. The implant can include an aperture or slot to be delivered via a guidewire or elongate light guide member, as described in the incorporated references.

In one embodiment, the implant includes a rigid housing body with large apertures therethrough where a cam member is extended and retracted. The housing body and cam can have interlocking recesses with openings that diverge inwardly beginning at and extending inwardly from the outer surface. The interlocking recesses do not pass completely through implant housing, cam, or plate. A rotatable plate can be pivotally attached to an end of the housing body. The rotatable plate normally is in a stowed position (e.g., aligned) in which the plate wing is aligned with the housing body. The wings of the rotational plate are in this aligned orientation when the implant is inserted through an opening made in a disc and through a rupture in the disc such that wings and rotational plate are positioned outside and adjacent the disc rupture or opening. After the implant is positioned, the rotatable plate is rotated 90 degrees to the deployed position. When the wings of the rotational plate in the deployed position are angled or perpendicular to the housing, they can seal, partially or completely, the rupture and opening, respectively, in the disc annulus. The rotational plate can be secured to the spine by the wings being fastened to adjacent vertebrae. The wings of the rotational plate can be affixed by screws, bone, adhesive, or other fasteners or fastening material being inserted through apertures in the wings of the rotational plate and secured to the vertebrae.

Another principal embodiment of the invention provides the implant housing, cam, and/or rotatable plate having grooves (e.g., Ω-shaped recesses) and inserts that can be hemophilic, hydrophilic, and attract and draw blood, fluids, and solids (using viscoelasticity and/or negative pressure) into the interior of the groove. The narrower outer opening in a groove creates an environment of lower pressure when a fluid flows through the opening (like a volume of water passing through a narrow opening is under less pressure than the same volume of water traveling through a wider opening). Bernoulli's Principle states that as the speed of a moving fluid increases, the pressure within the fluid decreases. As fluid, tissue, or materials flow faster through the narrower portions of a groove or implant, the pressure actually decreases rather than increases, facilitating ingrowth into the implant. Likewise, the pressure on the surface of the implant is less than the pressure within the implant, reducing subsidence of the implant into the vertebra. The grooves are shaped and dimensioned to also allow faster healing by allowing tissue to flow (ingrow) rapidly (through the narrower opening with lower pressure) and slow within the larger opening preventing the tissue from escaping once entering the implant. Likewise, materials inserted into the groove or implant are secured within the implant. Less force is also required to insert the implant as pressure is transferred from the surface to the inside of the groove or implant. The wider interior opening of the groove (inside the implant) has a greater volume and higher pressure than the outer opening when a material is flowing through the outer opening into the interior of the groove. When the grooves are sufficiently small, fluid flows into the grooves under capillary action due to a combination of liquid surface tension and the adhesion of the liquid to the surface of the groove. When materials (disc, vertebral, cement, fluids, solids, etc.) are viscoelastic, the diverging interior opening in a groove allows materials to expand (due to lower pressure) to interlock with the interior of the implants provided herein. Grooves can be oriented in any direction in the implant housing, cam, and/or plate. By way of example, and not limitation, grooves can be vertically, horizontally, obliquely, diagonally, and tangentially oriented and can, with respect to one another, be offset, co-linear, spaced apart, angled, etc.

Inserts can be provided within the grooves or apertures, recesses, or cavities of the implant. The inserts can be configured to be exposed to bone when implanted such that bone grows into the insert. Also, the inserts can be entirely solid, partially solid, hollow, and can be applied to a groove by any method of manufacturing including spray coating, electrolysis, macro-technology, microtechnology, nanotechnology, etc.

Grooves can be formed in the surface of an implant housing, cam, engaging surfaces, and/or rotational wing in any desired direction, spacing, or size. One preferred method of manufacture is forming linear, parallel, evenly-spaced grooves on the surface or portion of an implant. Another preferred method of manufacture is spacing the grooves unevenly (for instance, logarithmically) along the surface or at least another portion of implant. Unevenly spacing grooves provides for increased (or decreased) ingrowth at specific areas on an implant. For example, logarithmically spacing grooves on an implant incrementally distributes the pressure along an implant to reduce friction, stress, and strain on the implant. The shape and dimension of a groove can also vary along the length of a single groove. While the shape and dimension of grooves can vary as desired, the grooves preferably have outer surface openings with a width in the range of 1 micron to 5000 microns, and can also have a maximum interior width of 1 micron to 500 microns, or greater.

Grooves are preferably oriented linearly or arcuately, or configured as sequential arcs, ellipses, circles with similar or variable densities, parallel or undulating, or in any desired configuration to steer the implant along any desired path of travel. Any shaped wire or elongate guide (with or without light) can be operably coupled to a groove or grooves to steer the implant along a desired path of travel. In another embodiment in at least one portion of the implant the grooves are parallel (either linear or arcuately formed) and then change orientation. For example, but not limitation, the grooves can be at the leading edge of the implant directing the implant to a desired location intermediate two vertebrae and with teeth deployable by a cam or otherwise, or fixed at a trailing portion of the implant to insert the nose of the implant and stop and fix the tail of the implant intermediate two vertebrae. One preferred embodiment includes an implant with a smooth low-friction portion and a grooved higher-friction portion and/or a toothed highest-friction portion. Another embodiment provides an implant with a low-friction leading portion or nose that is smooth or with grooves parallel to the direction of insertion, a second portion with grooves similar or different than the first portion to redirect the second portion with regard to the first portion, and can also include a third portion with teeth (deployable or fixed) to hold the implant in position. Implant portions can also include at least one smooth low-friction surface and at least one higher-friction surface either grooved and/or a toothed higher-friction surface. Likewise, an implant with a smooth portion functions as a low-friction moveable surface. An implant with a grooved surface functions as a slightly higher-friction moveable surface (compared to the smooth surface) when the groove is parallel to the direction of travel. An implant with a grooved surface functions as an even higher-friction moveable surface (compared to the parallel grooved surface) when the groove is angled to the direction of travel. An implant with a grooved surface functions as an even higher-friction immovable surface (compared to the angled grooved surface) when the groove is normal to the direction of travel. An implant with a toothed portion functions as an even higher-friction surface (compared to the grooved surface that is normal to the direction of travel) to hold or fix the implant and prevent the implant from moving.

Another embodiment of the invention provides an implant for deposition intermediate two vertebrae wherein said implant can include an engaging surface with at least one recess, aperture, tooth, or wing that is textured to provide for tissue attachment. The recess can be part of a tooth, adjacent a tooth, on the engaging surface of the implant, through at least a portion of the implant, or completely through the implant. The recess, tooth, aperture, or wing can be textured by any desired method. Some preferred methods include chemical (acid) etching, laser etching, grit or sand blasting, electrolysis, etc. Texturing can be an additive coating or a subtractive process as described. Texturing is believed to aid in tissue attachment to the implant's surface as well as to the interior of the implant where material such as bone graft is packed or placed within the apertures. Texturing the implant provides for a bioactive surface to attract tissue inside the implant by providing a favorable charge or altering the pressure within the implant, as is the case with openings that diverge inwardly, and providing a scaffold for tissue migration inside the implant. Combining textures with teeth and/or apertures that diverge inwardly provides an immediate (on growth) and delayed (ingrowth) element to stably fix an implant. Teeth can be deployable, fixed, resorbable, porous, etc. The implant can be expandable, contractable, articulated, flexible, or fixed. Apertures can be variable or fixed, variable as the implant opens or closes. The implant or any elements described herein can be flexible, like a spring, rigid, or otherwise. Any material can be used to construct the implant, but presently preferred materials include, but are not limited to, polymers, metals (titanium, alloys, etc.), composites, hybrids, ceramics, bone, or other suitable materials. In one embodiment, the textures described in connection to the implant can be gradual, gradient, partial, full, and be applied randomly, evenly, or in any desired distribution.

The material used to make the implant can vary as desired, and include elastic, resilient, porous, or other materials. There are, for example, polymers available that produce a rigid, hard implant generally comparable to that produced by porous metal. The presently preferred implant components are, however, solid and substantially rigid, as well as being relatively hard, in the manner of metal. The implant can be grooved, channeled, recessed, or otherwise shaped and dimensioned to allow flexibility of rigid materials.

In another embodiment of the invention, implants are manufactured by combining two or more materials with different densities. By way of example, and not limitation, porous material and solid nonporous materials are blended together to form a density gradient in an implant. The blended gradient can be linear, where the implant density changes gradually at a constant rate across the body of the implant, or can be nonlinear, where the implant density changes at a non-constant rate across the body of the implant. An exponential rate of density change is an example of a non-constant density rate change. Another example of blending materials of different densities is combining polymer with metal, polymer with ceramic, polymer with bone, etc. Another example of blending materials of different densities is to layer a material of one density adjacent a material of another density. Moving from a layer of one density to a layer with another density can, in comparison to the density gradients described above, provide an instant, distinct, readily recognizable change in density. In one example, the cam body, engaging surface, or engaging members can be of different materials from the housing. The plate may be the same or different material of the cam or housing.

The cam or engaging surface can have a recess, hole, or other cavity. This recess, hole, or other cavity can be empty or filled. The recess, hole, or other cavity can be at least partially filled with porous bone, porous metal (e.g., titanium, tantalum, etc.), porous ceramics, or other materials that may or may not have bone growth factors for ingrowth of bone or other tissues into the cam or engaging surface. Such ingrowth of bone can form an interlock when the recess, hole, or other cavity has a diverging or shelf shape. The engaging surface of the housing and plate may also have the engagement members and/or pores or materials.

In one embodiment, the implant can be implanted by a method of implantation that includes: obtaining an implant having one or more apertures; obtaining one or more fasteners that fit into the one or more apertures; and inserting one of the fasteners into one of the apertures into a vertebral bone.

In one embodiment, the implant described herein can be implanted into a disc space between adjacent vertebrae. The implant may be inserted into a disc, or the disc space may be devoid of a disc. The implant may be inserted between a disc and a vertebra. The implant can be inserted when the implant has the cam and engagement surfaces in the retracted position. Once the implant is in the proper or desired location, the cam can be rotated so as to change the cam of the implant from a retracted position to a protruding position. The retracted position has the cam recessed in an opening or aperture of the housing. The protruding position can have the cam protruding from the opening or aperture of the housing. The rotation of the cam can either press against the adjacent vertebrae or press into the surface of the adjacent vertebrae. The vertebrae can be cammed as desired. The optional rotational plate can then be rotated to a position within and between the adjacent vertebrae or external to a perimeter surface of the adjacent vertebrae. Fastening members, such as bone screws, can then be inserted through apertures in the housing and/or rotational plate, where the apertures can have cooperative threading with the bone screw. One or more of the fasteners can have backwards threading where clockwise loosens and counterclockwise tightens.

As described herein, "indirect decompression" pertains to methods and apparatus described herein for reducing the pressure generated by discs (bulges, tears, hernias, etc.), vertebrae (fractures, osteophytes, tumors, etc.), facets, ligaments, capsules, etc., on the nerves and nerve coverings (meninges, arachnoid, dura, etc.) of the spine and nervous system without directly removing (or by minimally removing) the offending structure from a patient's body. The apparatus and methods described herein are especially useful for indirect decompression of nerves or vessels when direct access to a disc herniation is not possible or is risky.

In another preferred embodiment of the invention an implant is provided sterile or sterilizable, either separate or in a kit as a peel pack or other packaging, along with insertion instruments described herein that can be disposable or multiple use. Such instruments described herein include one of a group, but not limited to a light guide, elongate guide unit, implant delivery unit, dilater, tissue separation instrument, tissue removal instruments, and/or instruments or implants to alter the tilt or rotation of the vertebra or change the shape of the disc. The implant can be as described herein with the cam and/or rotatable plate.

In a further embodiment of the invention, provided is an improved method for fixing an implant adjacent tissue in the body of a patient. The method comprises the steps of forming an implant with an outer surface having at least one opening that expands in size as the distance from the outer surface into the opening increases; and, inserting the implant adjacent viscoelastic tissue in the body to permit the tissue to move into the opening and expand inside the opening.

In yet a further embodiment of the invention, provided is a method for securing an implant between an opposing pair of joint members. The method comprises the steps of providing a winged implant with at least one wing movable between a stowed position and a deployed position; providing the winged implant with the wing is the stowed position; inserting the winged implant between the opposing pair of joint members; and, moving the wing from the stowed position to the deployed position.

In still another embodiment of the invention, provided is an improved implant for disposition in an intervertebral disc space intermediate a pair of opposing vertebra in a spine having a longitudinal axis, the vertebra initially spaced apart an original distance, DO, prior to disposition of the implant. The disc space includes a height, a width, and an initial pressure, PO, prior to disposition of the implant. The implant comprises a structure with a top; a bottom; an outer surface to contact at least one of the pair of vertebrae; at least one interlocking elongate slot including an opening at the outer surface. The slot diverges inwardly away from the outer surface; extends at least partially through the body; and, begins at the outer surface to diverge inwardly. The implant has a height sufficient when disposed in the disc space to increase the distance between the vertebra by a distance ▲D sufficient to reduce while the vertebra are being separated the pressure by an amount ▲P less than the initial pressure PO. The implant has a first density. A tubular metallic marker is in the slot and has a second density greater than said first density. The marker can be porous. The implant can be substantially rigid and can include a rotatable wing. The area of the opening can be less than the area of the outer surface. The outer surface can be shaped and dimensioned to interlock at least one of the pair of vertebrae when the implant is inserted therebetween. The implant can be shaped and dimensioned such that when the implant is disposed intermediate said vertebra the wing is positioned outside the disc space. The implant can include fixation means to secure the wing to at least one of the vertebra. The implant can telescope. The can have at least tow operative positions. The marker can have a smooth surface extending across said opening. The implant can include a plurality of unidirectional parallel interlocking elongate slots. When the marker is porous, the openings in the marker can be shaped and dimensioned to draw in portions of the pair of vertebrae by negative pressure; and, the openings can each have a width in the range of 100 microns to 500 microns.

In yet still another embodiment of the invention an implant is provided for indirect decompression of nerves adjacent a disc space by disposition into an intervertebral disc space intermediate a pair of opposing vertebra in a spine having a longitudinal axis. The vertebra are initially spaced apart an original distance prior to disposition of the implant. The disc space includes a height, a width, and an initial pressure prior to disposition of the implant. The implant comprises a structure with a top; a bottom; an outer surface to contact at least one of the pair of vertebrae; at least one interlocking opening at the outer surface, the opening diverging inwardly away from the outer surface, extending at least partially through the body, and beginning at the outer surface to diverge inwardly; a height sufficient when disposed in the disc space to increase the distance between the vertebra sufficient to reduce the pressure by an amount less than the initial pressure; and, a first density. The implant also includes a marker having a second density different than said first density. The marker can be porous and/or substantially rigid. The implant can include a rotatable wing. The area of the opening can be less than the area of the outer surface. The outer surface can be shaped and dimensioned to interlock at least one of the pair of vertebrae when the implant is inserted there between. The implant can be shaped and dimensioned such that when the implant is disposed intermediate the vertebra the wing is positioned outside the disc space. The implant can include fixation means to secure the wing to at least one of the vertebra. The implant can open. The implant can have at least two operative positions. The marker can have a smooth surface extending across the opening. The implant can include a plurality of unidirectional parallel interlocking elongate slots. The openings in the porous marker can be shaped and dimensioned to draw in portions of the pair of vertebrae by negative pressure. The openings can have a width in the range of 1 microns to 5000 microns.

FIGS. 14 to 17 illustrate such an implant, generally indicated by reference character D10. Implant D10 is, as are each of the other implants herein, currently preferably made out of stainless steel or another metal. The material used to make implant D10 and the other implant illustrated herein can vary as desired, and include elastic or resilient or other materials. There are, for example, polymers available that produce a rigid, hard implant generally comparable to that produced by stainless steel. The presently preferred implant components are, however, metallic and substantially rigid, as well as being relatively hard, in the manner of stainless steel. Implant D10 includes a rigid stainless steel body D16 with large apertures D18 formed therethrough and with smaller openings D17. Each opening D17 diverges inwardly beginning at and extending inwardly from the outer surface D19. Openings D17 do not pass completely through implant D10, although such is possible. If an opening passing completely through implant D10, the tissue can be pressed through the top (or bottom) of the implant to the bottom (or top) and press against and meld or attach to the opposing vertebrae, which is presently not preferred. As is evident from various other implants illustrated herein, each opening D17 preferably, although not necessarily, includes an edge D20. Edges 20 function like teeth and tend to grip intervertebral and/or discal tissue that is pressed into diverging openings D17 when an implant D10 is inserted in an annulus (or between a pair of vertebrae if the disc is removed) and is compressed between a pair of vertebrae. Rotatable wings D11, D12 are each pivotally attached to a different one of the ends of body D16. Each wing D11, D12 normally is in a stowed position in which the wing is aligned and in registration with body D16 in the manner illustrated in FIG. 15. Wings D11, D12 are in this aligned orientation when implant D10 is inserted through an opening made in a disc and through a rupture in the disc such that wing D11 is positioned outside and adjacent the rupture and wing D12 is positioned outside and adjacent the opening. Consequently, implant D10 extends completely through the disc and the end of body D16 extend outwardly through the annulus via said opening or said rupture. After implant D10 is so positioned, wing D11 is rotated ninety degrees in the direction of arrow D24 to the deployed position illustrated in FIG. 14 and wing D12 is rotated ninety degrees in the direction of arrow D25 to the deployed position illustrated in FIG. 14. When wings D11 and D12 are in the deployed position of FIGS. 14, 16, and 17, they seal, partially or completely, the rupture and opening, respectively, in the disc annulus. If desired, screws, bone, adhesive, or other fasteners or fastening material can be inserted through apertures D26 and D27 in wing D12 to secure wing D12 in position. Screws inserted through apertures D26 and D27 would turn into vertebrae D14 and D15, respectively. One or more apertures comparable to apertures D26 and D27 can, if desired, be formed in wing D11 to secure wing D11 to vertebrae D14, and D15. The disc positioned between vertebrae D14 and D15 is omitted from FIGS. 14 to 17 for sake of clarity.

Bernoulli's Principle states that as the speed of a moving fluid increases, the pressure within the fluid decreases. As fluid or tissue or materials flow faster through the narrower portions of a groove or implant, the pressure actually decreases rather than increases facilitating ingrowth into the implant. Likewise the pressure on the surface on the implant is less than the pressure within the implant reducing subsidence of the implant into the vertebra. The grooves are shaped and dimensioned to also allow faster healing by allowing tissue to flow (in grow) rapidly (through the narrower opening with lower pressure) and slow within the larger opening preventing the tissue from escaping once entering the implant. Likewise materials inserted into the groove or implant are secured within the implant. Less force is also required to insert the implant as pressure is transferred from the surface to the inside of the groove or implant. The wider interior opening of the groove (inside the implant) has a greater volume and higher pressure than the outer opening when a material is flowing through the outer opening into the interior of the groove. When the grooves are sufficiently small, fluid flows into the grooves under capillary action due to a combination of liquid surface tension and the adhesion of the liquid to the surface of the groove. When materials (disc, vertebral, cement, fluids, solids, etc.) are viscoelastic, the diverging interior opening in a groove allows materials to expand (due to lower pressure) to interlock with the interior of the implants provided herein. Grooves can be oriented in any direction in the implant. By way of example, and not limitation, grooves can be vertically, horizontally, obliquely, diagonally, and tangentially oriented and can, with respect to one another, be offset, co-linear, spaced apart, angled, etc. Inserts within the grooves can be entirely solid, partially solid, hollow, and can be applied to a groove by any method of manufacturing including spray coating, electrolysis, macro-technology, micro-technology, nano-technology, etc. Alternatively, the outer opening in a groove can have a constant diameter or width for a distance then widen like a keyhole. Grooves can be formed horizontally along the surface of the implant, can be formed vertically along the surface of the implant, or can be placed in any other desired orientation. In one embodiment of the invention, the grooves remain open when the implant is inserted between a pair of opposing vertebra. This permits vertebral tissue, disc tissue, or other materials to move into the grooves. Any materials can be applied to alter the surface texture of the grooves. Such materials can be applied by, for example, spraying nano-particles, etching, electrolysis, and or heat treatment.

Figure 18:
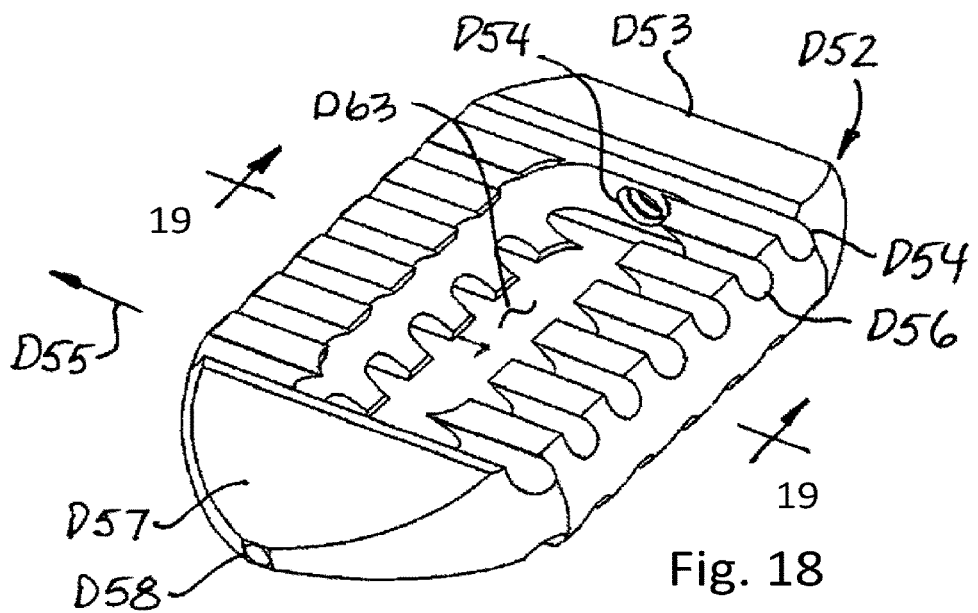
FIG. 18 provides a perspective view of an embodiment of an implant.
Figure 19:
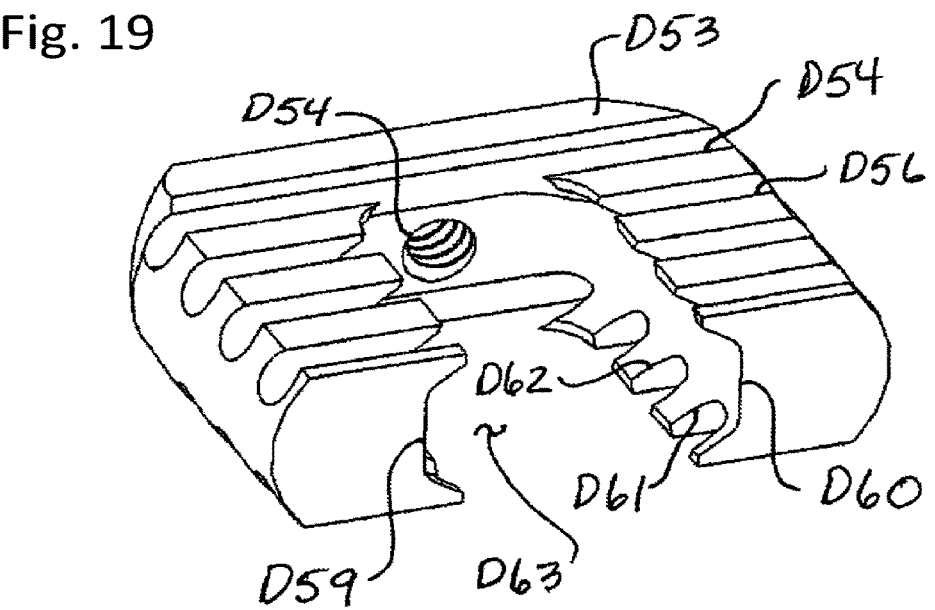
FIG. 19 provides a cross-sectional view of the implant of FIG. 18.

The "boat shaped" implant D52 illustrated in FIGS. 18 and 19 includes, as does implant D35, a plurality of parallel spaced apart grooves D54, D56, D61 formed on the top and bottom of implant D52. The parallel configuration of grooves D54, D56, D61, D62 facilitates the insertion of implant D52 between a pair of vertebra in the direction of arrow D55 (FIG. 18), or in a direction normal to arrow D55. Alternatively, the outer opening of each groove can have a constant diameter or shape for a distance and can thereafter widen like a keyhole. Grooves can be formed horizontally along a surface of the implant, can be formed vertically along a surface of the implant, and/or can be formed in any desired orientation, particularly to facilitate the growth of bone into at least a portion of the grooves. If the density or other physical property of the bone enables it to be distinguished from the implant, radiography can be used to detect the ingrowth of bone in a groove. The size of each groove D54, D56, D61, D62 preferably, although not necessarily, initially increases or widens as the depth of the groove D54, D56, D61 from the outer surface of implant D52 increases. Aperture D58 extends through the tapered tip D57 of the implant and into the aperture that is formed through the center of implant D52. Internally threaded aperture D58 also opens into the aperture that is formed through the center of implant D52 and extends completely through the end D53 of implant D52. As a result, implant D52 can slide along a wire that extends through aperture D58, through the central aperture in implant D52, and through aperture D54. A wire can be constructed of a material similar to or different from that of the implant to help visualize radiographically the position of the implant along the wire. The wire can be optical cable for transmitting light, or can be constructed to conduct electricity to determine the location of a nerve. The section view of FIG. 19 further illustrates the configuration of the aperture D63 extending through the center of implant D52. Aperture D63 is bounded by generally U-shaped sides D59 and D60 which function to gather, capture and contain materials within aperture D63. Any material or method can be utilized to alter the surface texture of aperture D63. One such material comprises nano-particles. Methods utilized at alter the surface texture include spraying, etching, electrolysis, and heat treatment. Apertures and grooves can be placed eccentrically in or through the tip D57 to facilitate inserting implant D52 by dissecting or dilating openings in an intervertebral disc (or in adjacent tissue like muscle, skin, or fascia).

In another embodiment of the invention, implants are manufactured by combining two or more materials with different densities. By way of example, and not limitation, porous material and solid non-porous materials are blended together to form a density gradient in an implant. The blend gradient can be linear, where the implant density changes gradually at a constant rate across the body of the implant, or can non-linear, where the implant density changes at a non-constant rate across the body of the implant. An exponential rate of density change is an example of a non-constant density rate change. Another example of blending materials of different densities is combining polymer with metal, polymer with ceramic, polymer with bone, etc. Another example of blending materials of different densities is to layer a material of one density adjacent a material of another density. Moving from a layer of one density to a layer with another density can, in comparison to the density gradients described above, provide an instant, distinct, readily recognizable change in density.

The implant illustrated in FIG. 20 is positioned intermediate vertebra E18 and E19 and includes body E20 and wing E21 pivotally attached to one end of body E20. Pivoting element (wing E21) can function as a compression plate and provide counter traction against body E20 in order to counter the amount of force and pressure generated by inserting the implant of FIG. 20. Body E20 is similar to implant E70 illustrated in FIGS. 24 to 27. Externally threaded screw E25 turns into an aperture that is formed in body E20 in a location and manner comparable to internally threaded aperture E70A formed in one end of implant E70 in FIG. 27, i.e., such that wing E21 can rotate about screw E25 in the directions indicated by arrows E22. Screws E23 and E24 extend through (and may interlock with) apertures formed in wing E21 and are turned into vertebra E18. As is illustrated in FIG. 20, the screws E23 and E24 can angle away from one another so that if the head of one screw E24 turns out a short distance, it function to block the outward movement of screw E23. This makes it more unlikely that both screws E23 and E24 will work completely free from wing E21. Similarly, member E25 can block the outward movement of either screw E23, E24 or of body E20. The implant of FIG. 20 can be utilized after a disc is completely removed from between a pair of vertebra, or can be utilized after a portion of the annulus and nucleus is removed which is sufficient to permit insertion of the implant. An aperture parallel to the longitudinal axis of body E20 can be formed along the longitudinal axis of screw E25 such that a wire can slidably extend through and along the longitudinal axis of screw E25. Implant E26 depicted in FIG. 21 has a configuration comparable to that of the implant illustrated in FIG. 20 and includes body E27 and wing E28 pivotable on body E27 in the directions indicated by arrows E29. Screw E30 extending through the top of wing E28 extends into one vertebra E18, while screw E31 extend through the bottom of wing E28 extends into another vertebra E19. Parallel grooves E32, E33, E37 are formed in the top and bottom of the implant and can receive cylindrical members E34, E35. Members E34 and E35 can serve any desirable function such as functioning as markers which facilitate determining the location of implant E26 in the spinal column of a patient and such as facilitating the ingrowth of tissue into members E34, E35. When members E34 and E35 serve as markers, members E34 and E35 have at least one physical property (such as density) which differs from that of body E27 When members E34 and E35 serve to facilitate the ingrowth of tissue, members E34 and E35 may be porous or be formed from materials equivalent to those found in a disc or vertebra. Grooves E32, E33, E37 need not be parallel, but, as noted earlier, a parallel configuration of grooves E32, E33, E37 facilitates inserted of implant 26 in a direction parallel to the longitudinal axes of the grooves. Grooves and/or inserts can be formed along the length, height, and/or width of any of the implants described herein and can provide for ingrowth of vertebra E18, E19 (FIG. 20). The width of the grooves can vary, but presently preferably is in the range of 100 microns to 500 microns. Aperture E36 extends through implant E26 along the longitudinal axis E42 of implant E26 such that a wire can be slidably inserted through aperture E36 to facilitate insertion of the implant E26 between vertebra by sliding the implant along the wire. FIG. 22 illustrates the tapered implant E26 inserted intermediate a pair of vertebra E40 and E41. The disc intermediate vertebra E40 and E41 has been omitted for sake of clarity. The implant E26 can be utilized after a disc is completely removed from between a pair of vertebra, or can be utilized after a portion of the annulus and nucleus is removed which is sufficient to permit insertion of the implant. FIG. 23 illustrates the implant E26 inserted intermediate a pair of vertebra E43, E44. In FIG. 23, wing E28 has been rotated ninety degrees from the position of wing E28 in FIGS. 21 and 22, and apertures (not visible) have been formed through wing E28 and the portion of body E27 adjacent wing E28 such that screws E45 and E46 can, after both wing E28 and body E27 are positioned between vertebra E43 and E44, be inserted and extend upwardly and downwardly, respectively, into the bottom of vertebra E43 and the top of vertebra E44 in the manner illustrated in FIG. 23. In the embodiment of the invention illustrated in FIG. 23, both wing E28 and body E27 are between vertebra E43 and E44. In the embodiment of the invention illustrated in FIG. 22, wing E28 is not positioned between vertebra E40 and E41. Positioning wing E28 entirely intermediate two vertebra and within the intervertebral disc space provides for a lower profile of implant E26 and prevents wing E28 from contacting muscles and nerves. Wing E28 can be fully recessed (within the disc space), partially recessed, or not recessed (outside the disc space).

Implant E70 is illustrated in FIGS. 24 to 27 and includes parallel grooves E74, E76 formed in the top and bottom, respectively, implant E70. Parallel grooves E75, E 77 are also formed in the top and bottom, respectively, of implant E70. Grooves E75 are normal to grooves E74. Grooves can be formed in any direction along the length, width, or height of the implant. The preferred maximum interior width of the grooves is in the range of 100 microns to 500 microns. Grooves E77 are normal to grooves E76. The size of each groove E74, E75, E76, E77 preferably, although not necessarily, initially increases or widens as the depth of the groove from the outer surface of implant D70 increases. Apertures E71 and E72 (FIG. 24) are sized to slidably receive a wire which can extend through aperture E71, through aperture E73, and through internally threaded aperture E72 to enable implant E70 to slide, if desired, along a wire during insertion of implant E70 intermediate a pair of adjacent vertebra. Aperture E71 extends through the nose of implant E70. Aperture E72 extends through the rear of implant E70. Oval aperture E73 extends completely through the central area of implant 50. Apertures E71, E72, E73 can be offset from each other.

Figure 28:
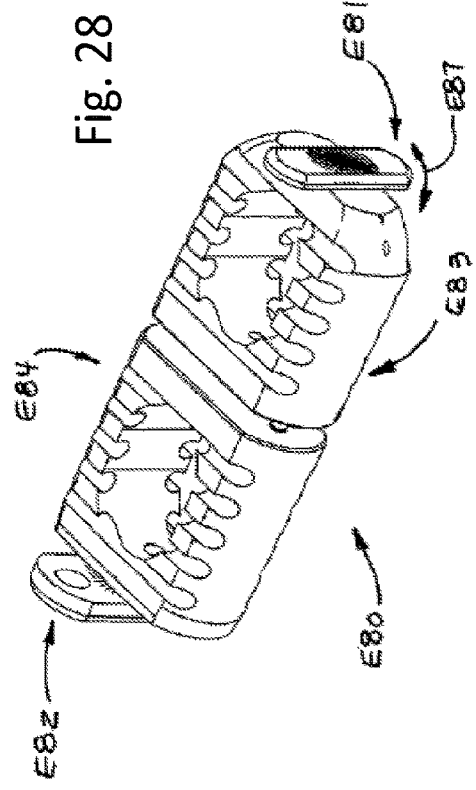
FIG. 28 provides a perspective view of an embodiment of an implant.
Figure 29:
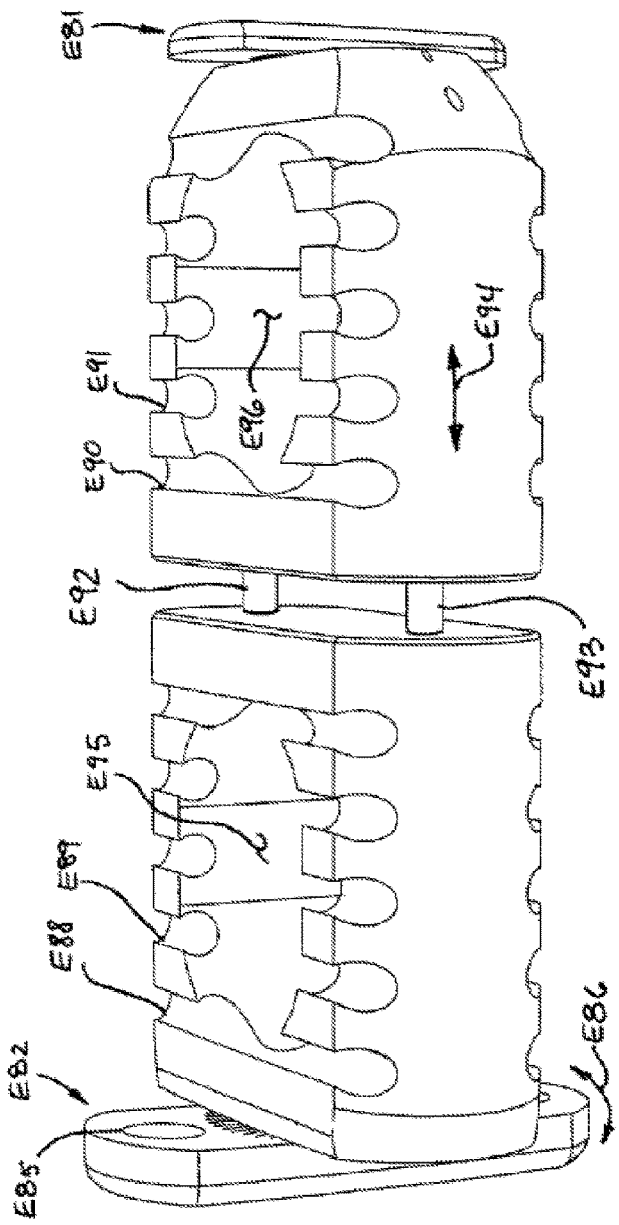
FIG. 29 provides another view of the implant of FIG. 28.

FIGS. 28 and 29 illustrate telescoping, winged implant E80. Implant E80 includes first E83 and second E84 body portions which telescope toward and away from each other in the directions indicated by arrow E94 (FIG. 29) along cylindrical pins E92 and E93. Body portion E83 includes parallel grooves E90, E91 formed in the top and bottom of portion E83. Similarly, body portion E84 includes parallel grooves E88, E89 formed in the top and bottom of portion E84. Oval aperture E95 extends completely through portion E84. Oval aperture E96 extends completely through portion E83. Wing E81 is pivotally mounted on portion E83 for rotation in the directions indicated by arrows E87. Wing E81 can rotate at least ninety degrees from the orientation illustrated in FIGS. 28 and 29, as can wing E82 mounted on portion E84. Apertures E85 are formed through wings E82 and E81 to receive a screw or other fastener that engages a vertebra or disc and anchor implant E80 in a desired position. Telescoping implant E80 by moving portions E83 and E84 together with a reversibly threaded member or any other means functions to draw wing E81 and wing E82 closer together. Drawing wings E81 and E82 together while either wing is positioned inside or outside a vertebra functions to draw disc, vertebral, or other tissues back into the disc. Drawing wings E81 and E82 together while either wing is positioned outside a vertebra also functions to change to orientation of a vertebra or draw two vertebra into alignment. Implant E80 can consist of more than two portions. Parallel pins E92, E93 can be tapered to limit or control the amount of telescoping of implant E80. Parallel pins E92, E93 can be configured to allow body portions E83, E84 to separate or collapse linearly or eccentrically allowing implant E80 to maintain a linear shape or to assume an arcuate shape. Body portions E83, E84 can be wedge shaped wherein collapsing said body portions E83, E84 produces an implant E80 with an arcuate shape. Portions E83 and E84 can be symmetric or asymmetric in shape. For example, portion E83 can be larger, smaller, or equal in size or shape to portion E84 in shape or size so that implant E80 (1) functions like a pivot to alter the cant or alignment of the vertebra, (2) expands the implant (spreads apart two adjacent shells in FIGS. 1-5), (3) alters the shape and dimension of the disc, or (4) changes the pressure intermediate two vertebra. Portions E83 and E84 can also be linear, offset, or angled from one another. An implant E80 with linear shape facilitates inserting implant E80 (or any of the implants described herein) along a straight guide unit. An implant E80 with an angular configuration can facilitate inserting implant E80 (or any of the implants described herein) (1) along a curvilinear path, (2) along a flexible guide unit, or (3) into the lower lumbar and sacral areas of the spine (that typically are blocked by the pelvis). An implant E80 with an angular configuration could better (1) conform to or change the shape of the disc or (2) alter the orientation of the vertebra. The angular shape of an implant E80 can extend along the height, length, or width of the implant. As noted, the grooves E90, E91 preferably formed in many of the implants described herein diverge, or widen, as the depth of the groove increases. Forming such grooves in an implant via a molding process is difficult, if not impractical. A preferred method of forming, for example, an implant comprises first molding the implant without the grooves formed therein. The grooves, etc. are then formed by first securing the implant in fixed position with a chuck or other apparatus, and by then utilizing a rotating drill bit or laser to cut through the implant. In another embodiment of the invention, after the implant is secured in fixed position, a drill bit is not utilized. Instead, a laser is utilized to cut a groove. Grooves can be formed in the surface of an implant in any desired direction, spacing, or size. One preferred method of manufacture is forming linear, parallel, evenly spaced grooves on the surface of an implant. Another preferred method of manufacture is spacing the grooves un-evenly (for instance, logarithmically) along the surface of implant. Unevenly spacing grooves provides for increased (or decreased) ingrowth at specific areas on an implant. Logarithmically spacing grooves on an implant incrementally distributes the pressure along an implant to reduce stress and strain on the implant. The shape and dimension of a groove can also vary along the length of a single groove. While the shape and dimension of grooves can vary as desired, the grooves preferably have outer surface openings with a width in the range of 100 microns to 500 microns, and can also have an maximum interior width of 100 microns to 500 microns, or greater.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art, all language such as "up to," "at least," and the like include the number recited and refer to ranges which can be subsequently broken down into subranges as discussed above.

Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An implant, comprising:
a rigid housing having a first end and a second end with a top side and bottom side therebetween, with at least one first opening in the housing in at least one of the top side or bottom side between the first end and second end, the at least one first opening having a first dimension from the top side to the bottom side that is smaller than a second dimension of the at least one first opening that is orthogonal to the first dimension, the first end having at least one second opening that extends into the at least one first opening, the at least one second opening having a longitudinal axis that is orthogonal with at least one of the first dimension and second dimension; and
at least one of the top side or bottom side having at least one engaging surface having an engaging opening formed into the at least one engaging surface, the engaging opening having a smaller cross-sectional profile at the at least one engaging surface that expands to a larger cross-sectional profile between the at least one engaging surface and a bottom of the engaging opening within the implant, wherein:
the implant includes at least two different densities that are formed in layers; and/or
the housing has a porous portion.

2. The implant of claim 1, wherein the at least one engaging surface has at least one engaging member configured for engaging tissue or bone.

3. The implant of claim 2, wherein the at least one engaging member includes an engaging tooth that is configured to penetrate into the tissue or bone and an engaging recess that is configured to receive tissue or bone therein.

4. The implant of claim 1, wherein the engaging opening in the at least one engaging surface is an engaging recess that is configured to receive tissue or bone therein.

5. The implant of claim 1, wherein the at least one first opening extends through the top side and through the bottom side, and a cam member is operably coupled with the housing, wherein the cam member includes a first engaging surface at a first cam end and a second engaging surface at a second cam end, both the first and second engaging surfaces being retracted in a first rotational position and being protruded in a second rotational position.

6. The implant of claim 1, the implant further comprising:
a retracted position having a cam member in a first rotational position with a cam surface retracted relative to the top side and bottom side; and
a protruding position having the cam member in a second rotational position with the cam surface protruding past at least one of the top or bottom side.

7. The implant of claim 6, wherein the first rotational position is 90 degrees of rotation from the second rotational position.

8. The implant of claim 1, further comprising a wing configured as a plate having a first plate surface operably coupled to the housing.

9. The implant of claim 8, wherein the plate has a porous portion.

10. The implant of claim 1, wherein the at least one engaging surface includes at least one engaging tooth that is configured to penetrate into the tissue or bone and at least one engaging recess that is configured to receive tissue or bone therein.

11. The implant of claim 10, wherein the at least one engaging recess is linear or arcuate.

12. The implant of claim 1, further comprising a cam body that has a first cam body lobe and an opposite second cam body lobe and a cam rotational axis therebetween, the first cam body lobe having a first engagement surface, the second cam body lobe having a second engagement surface, each engagement surface being on a perimeter of the cam body furthest from the cam rotational axis.

13. The implant of claim 1, further comprising a shaft with a head having a tool coupling member extending from the at least one second opening.

14. The implant of claim 1, further comprising a cam plate operably coupled with a shaft in the at least one second opening such that rotation of the shaft rotates the cam plate.

15. The implant of claim 1, further comprising a wing operably coupled to the housing.

16. The implant of claim 1, further including a cam member having a cross-sectional profile orthogonal with a longitudinal axis of the housing, the cross-sectional profile including a first cam dimension that is smaller than a second cam dimension.

17. The implant of claim 1, further comprising an opening having a side with a ridge.

18. The implant of claim 1, further comprising a growth factor to promote ingrowth into an opening in the implant.

19. The implant of claim 1, the implant including texturing to promote ingrowth into an opening in the implant.

20. The implant of claim 1, wherein the implant comprises a density gradient with a linear, non-linear, and/or exponential rate of density change.

21. A method of implanting an implant between two surfaces, the method comprising:
 inserting the implant of claim 1 into an intervertebral space between adjacent vertebrae.

22. The method of claim 21, further comprising fastening the implant to the adjacent vertebrae with a fastener for each vertebra.

23. An intervertebral implant, comprising:
a housing having a longitudinal axis between a first end and a second end with a top side and a bottom side therebetween, with at least one opening in at least one of the top side or bottom side, the implant having a first housing dimension from the top side to the bottom side that is smaller than a second housing dimension that is orthogonal to the first housing dimension and the second housing dimension is orthogonal with the longitudinal axis, and
a cam member operably and rotationally coupled to the housing and having a cross-sectional profile perpendicular to an axis of rotation of the cam member, wherein the cross-sectional profile includes a first cam dimension that is smaller than a second cam dimension, an engaging surface being located on a portion of the cam member that includes the second cam dimension, the first cam dimension being smaller than the first housing dimension and the second cam dimension being larger than the first housing dimension;
a cam plate having a first plate surface rotatably coupled to the first end of the housing, the cam plate having a plurality of fastener apertures configured for receiving fasteners therethrough, wherein the cam plate is rotationally mounted with respect to a shaft such that rotation of the shaft does not rotate the cam plate.

24. An intervertebral implant, comprising:
a housing having a first end and a second end with a top side and a bottom side therebetween, with at least one opening in the housing in at least one of the top side or bottom side between the first end and second end, the first end having a first opening that extends into the at least one opening;
an elongate shaft with a longitudinal axis located in the first opening so as to protrude therefrom and extend into the at least one opening; and
the housing having a density gradient with at least one porous engaging surface; and a cam member operably coupled to the elongate shaft, wherein the cam member has a cross-sectional profile perpendicular to an axis of rotation of the cam member, wherein the cross-sectional profile includes a first cam dimension that is smaller than a second cam dimension, wherein:
the implant includes at least two different densities that are formed in layers.

25. An implant, comprising:
a rigid housing having a first end and a second end with a top side and a bottom side therebetween, with at least one first opening in the housing in at least one of the top side or bottom side between the first end and second end, the at least one first opening having a first dimension from the top side to the bottom side that is smaller than a second dimension of the at least one first opening that is orthogonal to the first dimension, the first end having at least one second opening that extends into the at least one first opening, the at least one second opening having a longitudinal axis that is orthogonal with at least one of the first dimension and second dimension; and
at least one of the top side or bottom side having at least one engaging surface having an engaging opening formed into the at least one engaging surface, the engaging opening having a smaller cross-sectional profile at the at least one engaging surface that expands to a larger cross-sectional profile between the at least one engaging surface and a bottom of the engaging opening within the implant, wherein:
the engaging opening formed in the at least one engaging surface includes a maximum outer dimension between 1 micron and 5000 microns and a maximum interior dimension of 1 micron to 5000 microns.

26. An implant, comprising:
a rigid housing having a first end and a second end with a top side and a bottom side therebetween, with at least one first opening in the housing in at least one of the top side or bottom side between the first end and second end, the at least one first opening having a first dimension from the top side to the bottom side that is smaller than a second dimension of the at least one first opening that is orthogonal to the first dimension, the first end having at least one second opening that extends into the at least one first opening, the at least one second opening having a longitudinal axis that is orthogonal with at least one of the first dimension and second dimension; and
at least one of the top side or bottom side having at least one engaging surface having an engaging opening formed into the at least one engaging surface, the engaging opening having a smaller cross-sectional profile at the at least one engaging surface that expands to a larger cross-sectional profile between the at least one engaging surface and a bottom of the engaging opening within the implant, wherein:
the housing is expandable by including a first body portion and a second body portion, wherein at least one of the first body portion or second body portion is coupled with a plurality of pins such that the first body portion and second body portion can slide apart to expand the rigid housing.

* * * * *